United States Patent
Ley et al.

(10) Patent No.: US 8,679,461 B2
(45) Date of Patent: Mar. 25, 2014

(54) USE OF HESPERETIN FOR ENHANCING THE SWEET TASTE

(75) Inventors: Jakob Ley, Holzminden (DE); Guenter Kindel, Hoexter (DE); Susanne Paetz, Hoexter (DE); Thomas Riess, Holzminden (DE); Martin Haug, Noerdlingen (DE); Ralph Schmidtmann, Holzen (DE); Gerhard Krammer, Holzminden (DE)

(73) Assignee: Symrise AG, Holzminden (DE)

( * ) Notice: Subject to any disclaimer, the term of this patent is extended or adjusted under 35 U.S.C. 154(b) by 1137 days.

(21) Appl. No.: 11/996,765

(22) PCT Filed: Jul. 25, 2006

(86) PCT No.: PCT/EP2006/064633
§ 371 (c)(1),
(2), (4) Date: Aug. 8, 2008

(87) PCT Pub. No.: WO2007/014879
PCT Pub. Date: Feb. 8, 2007

(65) Prior Publication Data
US 2008/0305052 A1 Dec. 11, 2008

Related U.S. Application Data

(60) Provisional application No. 60/702,943, filed on Jul. 27, 2005, provisional application No. 60/784,444, filed on Mar. 22, 2006.

(51) Int. Cl.
*A61K 8/49* (2006.01)
(52) U.S. Cl.
USPC .......................................... 424/49; 426/536
(58) Field of Classification Search
None
See application file for complete search history.

(56) References Cited

U.S. PATENT DOCUMENTS

| 3,739,064 A | 6/1973 | Rizzi |
| 3,908,028 A | 9/1975 | Neely et al. |
| 4,055,678 A | 10/1977 | Crosby et al. |

| 2002/0188019 A1 * | 12/2002 | Ley et al. ...................... 514/456 |
| 2008/0242740 A1 | 10/2008 | Ley et al. |
| 2008/0305052 A1 | 12/2008 | Ley et al. |

FOREIGN PATENT DOCUMENTS

| EP | 1 177 728 A1 | 2/2002 |
| JP | 62051613 | 3/1987 |
| JP | 2003169631 A | 6/2003 |

OTHER PUBLICATIONS

"Volatile Components of Citrus Fruits. Characteristic Aroma Components of Ki-mikan (Ogon-kan) (Citrus flaviculpus Hort. ex Tanaka) Fruit," Katayama, S. and Iwabuchi, H., Foods Food Ingredients J. Japan 202: Abstract (2002).*
XP000002658955, Miyake T. et al., "Composition useful for e.g. foods, drinks, drugs or cosmetics, comprises 3-alpha-monoglucosylnanngin, containing nanngenin glycosides based on the monoglucosylnanngin," and JP 2002 199896 A (Hayashibara Seibutsu Kagaku) Jul. 16, 2002, WPI abstract.
Extended European Search Report (EP Appl. No. 10190555.2-2114 (Sep. 23, 2011)).

* cited by examiner

*Primary Examiner* — David J Blanchard
*Assistant Examiner* — Daniel F Coughlin
(74) *Attorney, Agent, or Firm* — Novak Druce Connolly Bove + Quigg LLP

(57) ABSTRACT

The use of hesperetin of formula (I) is described wherein the hesperetin of formula (I) is in the form of a (2S)-enantiomer, (2R)-enantiomer or any desired mixture of the two enantiomers, a salt of hesperetin of formula (I), —a mixture comprising or consisting of two or more salts of the hesperetin of formula (I), or a mixture comprising or consisting of hesperetin of formula (I) and one or more salts of hesperetin of formula (I) for enhancing the sweet taste of a sweet-tasting substance or sweet olfactory impression of a flavoring which gives a sweet olfactory impression.

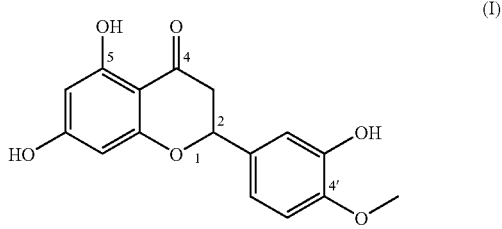

18 Claims, No Drawings

USE OF HESPERETIN FOR ENHANCING THE SWEET TASTE

RELATED APPLICATIONS

This application is a national stage application (under 35 U.S.C. §371) of PCT/EP2006/064633 filed Jul. 25, 2006, which claims benefit of U.S. Provisional application 60/702,943 filed Jul. 27, 2005 and U.S. Provisional application 60/784,444 filed Mar. 22, 2006.

The invention primarily relates to the use of hesperetin and/or the salts thereof for enhancing the sweet taste of sweet-tasting substances or the sweet olfactory impression of flavourings which give a sweet olfactory impression. The invention thus primarily relates to the use of said substances as sweetness enhancers. The invention also relates to specific preparations which contain an effective content of hesperetin and/or the salts thereof and to processes for enhancing the sweet taste of the sweet-tasting substance or the sweet olfactory impression of a flavouring which gives a sweet olfactory impression.

The invention has been developed in two stages. As a result of this development history the text at hand is divided into two parts. Part A describes the invention prior to further development, part B is a supplementary description of the invention following further development. However, obviously aspects only described in part A are also valid with respect to the invention following further development. Aspects from part B may also be combined with aspects from part A, in particular with respect to preferred embodiments of the invention.

PART A

Description of the Invention Prior to the Development

The invention relates to the use of hesperetin (4'-methoxy-3',5,7-trihydroxyflavanone) or the salts thereof for enhancing pleasant taste impressions, in particular sweet taste impressions. The invention also relates to specific preparations which contain an effective content of hesperetin and/or the salts thereof.

Foods (nourishment, including beverages) or semi-luxury foods (semi-luxuries) which have a high sugar content (primarily sucrose, lactose, glucose or fructose or mixtures thereof) are usually strongly preferred by consumers owing to their sweetness. On the other hand it is generally known that a high content of easily metabolisable carbohydrates allows the blood sugar level to greatly increase, leads to the formation of fatty deposits and can ultimately lead to health problems, such as excess weight, obesity, insulin resistance, late-onset diabetes and their secondary diseases. In particular there is also the aggravation that many of the above-mentioned carbohydrates can also affect dental health as they are broken down by specific types of bacteria in the oral cavity into lactic acid for example and can attack the tooth enamel of adolescent or adult teeth (cavities).

It has therefore long been an aim to reduce the sugar content of foods and/or semi-luxury foods to the absolutely necessary amount. A corresponding measure consists in the use of sweeteners. These are chemically uniform substances which do not themselves have a calorific value, or have only a very low calorific value, and simultaneously give a strong sweet taste impression. The substances are usually non-cariogenic (overview: Valerie B. Duffy, Madeleine Sigman-Grant, Margaret A. Powers, Denise Elmore, Esther F. Myers, Diane Quagliani, Marie Spano, Kimberly F. Stitzel, Sue Taylor, Robert Earl and Sonja Connor, *Journal of the American Dietetic Association* 2004, 104 (2), 255-275). Some of what are known as bulk sweeteners, such as sorbitol, mannitol or other sugar alcohols, are outstanding sweeteners and can also partially replace the remaining food technology-related properties of sugars, but too frequent intake leads to osmotically-induced digestion problems among some people. While, owing to their low concentration in use, the non-nutritive, highly intensive sweeteners are very suitable for bringing sweetness into foods, they often exhibit taste-related problems as a result of time-intensity profiles which are not similar to sugar (e.g. sucralose, stevioside, cyclamate), a bitter and/or astringent aftertaste (e.g. acesulfame K, saccharin), or pronounced additional flavour impressions (e.g. glycyrrhetinic acid ammonium salt). Some of the sweeteners are not particularly stable as regards heat (e.g. thaumatin, brazzein, monellin), are not stable in all applications (e.g. aspartame) and are sometimes very long-lasting in terms of their sweet effect (strong sweet aftertaste, e.g. saccharin).

An improvement in the taste properties, in particular the aftertaste problem of non-nutritive, highly intensive sweeteners, can be achieved by the use of tannic acid, e.g. as described in WO 98/20753, or phenolic acids as in U.S. Pat. No. 3,924,017. However, substances of this type are not particularly stable in applications owing to their catechol units.

A further possibility—without using non-nutritive sweeteners—consists in reducing the sugar content of food and/or semi-luxury foods and adding sensorily weak or imperceptible substances which indirectly or directly enhance the sweetness, as described for example in WO 2005/041684. The substances described in WO 2005/041684 are, however, explicitly of non-natural origin and are therefore more difficult to assess from a toxicological perspective than substances of natural origin, in particular if the latter occur in foods or semi-luxury foods or originate from raw materials for obtaining foods or semi-luxury foods. EP 1 291 342 A1 describes such substances of natural origin (pyridinium betaines). However, they do not selectively affect the sweet taste, rather other tastes, such as savouriness or saltiness, are affected. In addition, the disclosed substances can only be purified with high expenditure.

It is therefore desirable to find naturally occurring substances which, in low concentrations, effectively enhance the sweet taste impressions of sweet substances, in particular the sweet taste impression of reduced-sugar foods and semi-luxury foods, without adversely affecting the remaining flavour profile.

The primary object of the present invention was to find substances which (a) are selectively suitable for enhancing the sweet taste of a sweet-tasting substance, preferably without adversely affecting the remaining flavour profile, (b) can be widely used and (c) occur in foods or semi-luxury foods or the corresponding raw materials for the preparation thereof or are formed during the production of foods or semi-luxury foods.

The object posed is achieved according to the invention by (i) hesperetin of formula (I)

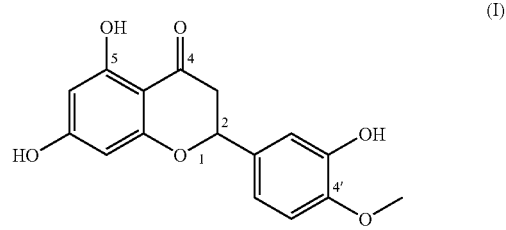 [SMILES: COc1ccc(C2CC(=O)c3c(O)cc(O)cc3O2)cc1O]

wherein the hesperetin of formula (I) is in the form of a (2S)-enantiomer, (2R)-enantiomer or any desired mixture of the two enantiomers,
and/or
(ii) the salts thereof
for enhancing the sweet taste of a sweet-tasting substance or sweet olfactory impression of a flavouring which gives a sweet olfactory impression.

The sweet taste of a sweet-tasting substance or the sweet olfactory impression of a flavouring which gives a sweet olfactory impression is preferably enhanced in a preparation used for nourishment, oral hygiene or consumption.

The use of the hesperetin or salts thereof to be used according to the invention for enhancing the sweet taste of a sweet-tasting substance or the sweet olfactory impression of a flavouring which gives a sweet olfactory impression is preferably in ready-to-consume foods and semi-luxury foods, wherein the concentration (i) of hesperetin and/or (ii) the salts thereof is less than 0.025% by weight, preferably less than 0.02% by weight, based on the total weight of ready-to-consume foods and semi-luxury foods.

Sweet-tasting substances (including natural sources of these substances) can for example be sweet-tasting carbohydrates or sugars (e.g. sucrose (synonymous with saccharose), trehalose, lactose, maltose, melizitose, raffinose, palatinose, lactulose, D-fructose, D-glucose, D-galactose, L-rhamnose, D-sorbose, D-mannose, D-tagatose, D-arabinose, L-arabinose, D-ribose, D-glyceraldehyde, maltodextrin) or vegetable preparations containing predominantly these carbohydrates (e.g. from sugar beet (*Beta vulgaris* ssp., sugar fractions, sugar syrup, molasses), from sugar cane (*Saccharum officinarum* ssp., e.g. molasses, sugar syrups), from sugar maple (*Acer* ssp.), from agave (agave thick juice), synthetic/enzymatic hydrolysates of starch or sucrose (e.g. invert sugar syrup, highly enriched fructose syrups made from corn starch), fruit concentrates (e.g. from apples or pears, apple syrup, pear syrup), sugar alcohols (e.g. erythritol, threitol, arabitol, ribitol, xylitol, sorbitol, mannitol, dulcitol, lactitol), proteins (e.g. miraculin, monellin, thaumatin, curculin, brazzein), sweeteners (magap, sodiumcyclamate, acesulfame K, neohesperidin dihydrochalcone, saccharin sodium salt, aspartame, superaspartame, neotame, alitame, sucralose, stevioside, rebaudioside, lugduname, carrelame, sucronon-ate, sucrooctate, monatin, phyllodulcin), certain sweet-tasting amino acids (glycine, D-leucine, D-threonine, D-asparagine, D-phenylalanine, D-tryptophan, L-proline), other sweet-tasting low-molecular substances (e.g. hernandulcin, dihydrochalcone glycosides, glycyrrhizin, glycyrrhetinic acid ammonium salt or other glycyrrhetinic acid derivatives), liquorice extracts (*Glycyrrhizza glabra* ssp.), *Lippia dulcis* extracts, *Momordica* ssp. extracts or individual substances (in particular *Momordica grosvenori* [Luo Han Guo] and the mogrosides obtained therefrom), *Hydrangea dulcis* or *Stevia* ssp. (e.g. *Stevia rebaudiana*) extracts or individual substances.

In salts of the hesperetin of the above formula (I) to be used according to the invention, one, a plurality of or all group(s) of the hesperetin that can be deprotonated are deprotonated. There is then an appropriate quantity of counterions, wherein these are preferably selected from the group comprising: single positively charged cations of the first primary and secondary group, ammonium ions, trialkylammonium ions, doubly positively charged cations of the second primary and secondary group and trebly positively charged cations of the third primary and secondary group and mixtures thereof.

Particularly preferred cations are $Na^+$, $K^+$, $NH_4^+$, $Ca^{2+}$, $Mg^{2+}$, $Al^{3+}$ and $Zn^{2+}$.

While U.S. Pat. No. 5,580,545 describes taste-altering properties, i.e. which increase the full-bodied taste and the acidic taste impression and reduce the salty taste impression in particular, for some flavones (2-phenylchrom-2-en-4-one), a sweet-enhancing effect was not disclosed.

U.S. Pat. No. 5,703,053 describes 5-hydroxyflavone and hesperidin (hesperetin-7-rutinoside) as masking agents for generally unpleasant taste impressions. A sweet-enhancing effect cannot be derived therefrom.

US 2002 188,019 describes hydroxy flavanones (2-phenyl-chrom-4-one) as effective bitterness masking agents and taste improvers even for the aftertaste from non-nutritive, highly intensive sweeteners. A sweet-enhancing effect is not described, however.

While *J. Agric. Food Chem.* 1981, 29, 305-312 mentions that hesperetin (compound 13a in this case) has a very weak sweet taste in a concentration of 200 ppm, a sweetness enhancement compared with other sweet-tasting substances as a result of the addition of low concentrations of hesperetin is not disclosed.

Surprisingly it has been found that the hesperetin or salts thereof to be used according to the invention also superproportionally increase(s) the sweet taste impression of sweet-tasting substances even in very low concentrations (less than 0.025% by weight, preferably less than 0.02% by weight), in particular however of sugars such as sucrose, lactose, glucose, D-tagatose and/or fructose (cf. in particular Examples 1 and 2) and it is thus possible to reduce the sugar content in corresponding foods and semi-luxury foods without reducing the sweet taste impression at the same time. In the low concentrations preferably used the hesperetin and/or the salts thereof used according to the invention exhibit(s) only a very weak inherent taste.

In contrast to the compounds naringenin, homoeriodictyol, eriodictyol and eriodictyol-7-methylether characterised in US 2002 188,019 as preferred bitterness masking agents and taste-improving compounds, hesperetin has a clear and significant sweet-enhancing effect (cf. Example 1). The same applies to the salts of hesperetin.

Hesperetin occurs as a free compound primarily in exudates of sclerophyllous evergreen plants. It was described thus e.g. in *Artemisia xanthochroa* (J. Jakupovic, R. X. Tan, F. Bohlmann, Z. J. Jia and S. Huneck, *Phytochemistry* 1990, 29, 3683-3685) and in *Chysothamnus* ssp. (J. F. Stevens, E. Wolenweber, M. Ivancic, V. L. Hsu, S. Sundberg and M. L. Deinzer, *Phytochemistry* 1999, 51, 771-780). It may also be found as a catabolic product of hesperidin and/or neohesperidin in citrus products (Angel Gil-lzquierdo, Maria I. Gil, Federico Ferreres and Francisco A. Tomas-Barberan, *J. Agric. Food Chem.* 2001, 49 (Part 2), pages 1035-1041).

As already mentioned, one aspect of the present invention relates to the use of a hesperetin of formula (I) or of a corresponding salt for enhancing the sweet taste of a sweet-tasting substance, i.e. as a taste corrigent.

The hesperetin and/or the salts thereof are preferably used in a preparation used for nourishment, oral hygiene or consumption, wherein the preparation includes one or more sweet-tasting substance(s).

A further aspect of the invention relates to a preparation used for nourishment, oral hygiene or consumption, comprising (i) hesperetin of formula (I)

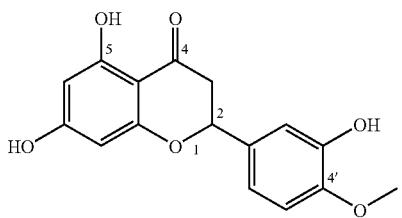

(I)

wherein the hesperetin of formula (I) is in the form of a (2S)-enantiomer, (2R)-enantiomer or any desired mixture of the two enantiomers,
and/or
(ii) the salts thereof
and
one or more further (iii) sweet-tasting substance(s) and/or (iv) flavouring(s) which give(s) a sweet olfactory impression, wherein the quantity of (i) hesperetin and (ii) the salts thereof in the preparation is sufficient to enhance in sensory terms the sweet taste impression of the sweet-tasting substance(s) or the sweet olfactory impression of the flavouring(s) which give(s) a sweet olfactory impression. It is therefore possible to reduce the content of one or more of the sweet-tasting substance(s), but in particular of sugars such as sucrose, lactose, fructose and/or glucose or the mixtures thereof by 5 to 60% (based on the sweet-tasting substance(s)), compared to a preparation without (i) hesperetin or (ii) the salts thereof, without the sweet taste impression being reduced in the process.

Preferred therefore are (sugar-reduced) preparations according to the invention, which as a sweet-tasting substance or sweet-tasting substances include one or more sugar(s), wherein the quantity of (i) hesperitin or (ii) the salts thereof is sufficient to impart the same or an enhanced sweet impression, compared with a preparation which, with an otherwise identical composition, contains neither (i) hesperetin nor the salts thereof but at least 1.05 times, preferably at least 1.4 times, the amount of sugar. The sugars are preferably selected in this case from the group comprising: sucrose, lactose, glucose, fructose and mixtures thereof.

Flavourings which give a sweet olfactory impression are flavourings which do not taste sweet in the narrower sense but can suggest a sweet taste in the wider sense (including odour perception). Flavourings of this type are in particular: vanillin, ethylvanillin, Furaneol® (2.5-dimethyl-4-hydroxy-3 (2H)-furanone) and derivatives, maltol and derivatives (e.g. ethylmaltol), cumarine, deltalactones (e.g. 4-methyldeltalactone, massoilactone, deltadecalactone, tuberolactone), methyl sorbate, divanillin, 4-hydroxy-2(or 5)-ethyl-5(or 2)-methyl-3(2H)furanone, 2-hydroxy-3-methyl-2-cyclopentenone, 3-hydroxy-4,5-diemethyl-2(5H)-furanone, fruit esters and phenylacetaldehyde.

The quantity of (i) hesperetin and (ii) the salts thereof in the preparation is preferably sufficient to significantly enhance the sweet taste or olfactory impression by at least 10%, based on a comparative formulation which, with an otherwise identical composition, includes neither hesperetin nor the salts thereof.

Reference has already been made above to the fact that free hesperetin, i.e. without a sugar residue as in hesperidin or neohesperidin, occurs in natural products, primarily in exudates of sclerophyllous evergreen plants and as a catabolic product of hesperidin and/or neohesperidin in citrus products. The preparations according to the invention are not naturally occurring products of this type. It should be noted in this regard that in the naturally occurring products the quantity of (i) hesperetin and (ii) the salts thereof is usually not sufficient to significantly enhance in sensory terms the sweet taste impression of a substance in the naturally occurring product or the sweet olfactory impression of a flavouring in the naturally occurring product which gives a sweet olfactory impression.

In particular the quantity of (i) hesperetin and (ii) the salts thereof in the naturally occurring product is not sufficient to enhance the sweet taste or olfactory impression, and it is thus not possible to significantly reduce the content of one or more of the sweet-tasting substances, but in particular of sucrose, lactose, fructose, glucose or mixtures thereof, e.g. by 5 to 60% (based on the sweet-tasting substance) without the sweet taste impression being reduced in the process.

According to the above statements, in a preparation according to the invention the hesperetin and/or the salts thereof is/are preferably not in the form of (a) an exudate of a sclerophyllous evergreen plant, in particular *Artemisia xanthochroa* or *Chysothamnus* ssp., and is not present (b) together with other flavanones as a constituent of the same citrus product.

Particularly relevant are preparations according to the invention which include at least one sweet-tasting substance, preferably a sugar such as sucrose, lactose, glucose and/or fructose, wherein the quantity of sweet-tasting substance is not sufficient to be perceived in a comparative preparation, which does not include hesperetin, salt or a mixture thereof but otherwise has an identical composition, as a satisfactory sweet taste, and the quantity of hesperetin, salts or mixture thereof in the preparation is sufficient to enhance in sensory terms the sweet taste impression of the sweet-tasting substance.

The preparations according to the invention used for nourishment or consumption are e.g. bread, cakes and pastries (e.g. bread, biscuits, cake, other bakery items), confectionery (e.g. chocolates, chocolate bar-type products, other bar-type products, fruit gums, hard and soft toffees, chewing gum), alcoholic or non-alcoholic drinks (e.g. coffee, tea, wine, wine-containing drinks, beer, beer-containing drinks, liqueurs, schnapps, brandies, fruit-containing soft drinks, isotonic drinks, soft drinks, nectars, fruit and vegetable juices, fruit or vegetable preparations), instant drinks (e.g. instant cocoa drinks, instant tea drinks, instant coffee drinks), meat products (e.g. ham, fresh sausage or raw sausage preparations, pickled or marinated fresh or salt meat products), eggs or egg products (dried egg, egg white, egg yolk), cereal products (e.g. breakfast cereals, muesli bars, pre-cooked finished rice products), milk products (e.g. milk drinks, dairy ice cream, yoghurt, kefir, cream cheese, soft cheese, hard cheese, dried milk powder, whey, butter, buttermilk, partially or wholly hydrolysed milk protein-containing products), products made of soya protein or other soybean fractions (e.g. soya milk and products produced therefrom, soya lecithin-containing preparations, fermented products such as tofu or tempe or products produced therefrom, soya sauces), fruit preparations (e.g. preserves, sorbets, fruit sauces, fruit fillings), vegetable preparations (e.g. ketchup, sauces, dried vegetables, frozen vegetables, pre-cooked vegetables, vegetables pickled in vinegar, preserved vegetables), snacks (e.g. backed or fried potato crisps or potato dough products, bread dough products, extrudates based on maize or peanut), products based on fat or oil or emulsions thereof (e.g. mayonnaise, remoulade, dressings, spice preparations), other ready-to-eat meals and soups (e.g. dried soups, instant soups, pre-cooked soups), condiments, spice mixtures and in particular seasonings which are used for example in the snacks sector.

Preparations according to the invention can be in the form of semi-finished products, perfume, flavouring or flavour compositions or a spice mixture.

Preparations according to the invention which are used as semi-finished products preferably contain a total of 0.0001% by weight to 95% by weight, preferably 0.001 to 80% by weight, but in particular 0.01% by weight to 50% by weight, based on the total weight of the preparation, of the hesperetin of formula (I) and/or the salts thereof to be used according to the invention.

Preparations according to the invention can in particular be used as semi-finished products for producing further preparations used for nourishment or consumption, in particular in spray-dried form. Preparations according to the invention can also be in the form of capsules, tablets (uncoated and coated tablets, e.g. gastric juice-resistant coatings), sugar-coated pills, granules, pellets, solid mixtures, dispersions in liquid phases, emulsions, powders, solutions, pastes or other preparations that may be swallowed or chewed as food supplements.

The preparations according to the invention used for oral hygiene are in particular oral and/or dental care products, such as toothpastes, tooth gels, tooth powder, mouthwashes, chewing gums and other oral hygiene products.

Further conventional active ingredients, raw materials, auxiliaries and additives for preparations used according to the invention for nourishment, oral hygiene or consumption can be provided in quantities of 5 to 99.999999% by weight, preferably 10 to 80% by weight, based on the total weight of the preparation. The preparations may also contain water in a quantity up to 99.999999% by weight, preferably 5 to 80% by weight, based on the total weight of the preparation.

The preparations according to the invention containing hesperetin and/or the salts thereof are produced according to a preferred embodiment by incorporating the hesperetin of formula (I) and/or the salts thereof as a substance, as a solution (e.g. in ethanol, water, 1,2-propylene glycol, dimethylsulphoxide) or in the form of a mixture with a solid or liquid carrier (e.g. maltodextrin, starch, silica gel), flavours or flavourings and optionally further auxiliaries and/or stabilisers (e.g. natural or synthetic polysaccharides and/or plant gums, such as modified starches or gum arabic) in a base preparation used for nourishment, oral hygiene or consumption. Preparations according to the invention in the form of a solution and/or suspension or emulsion may advantageously also be converted by spray drying into a solid preparation according to the invention (semi-finished product).

Spray-dried, solid preparations according to the invention preferably contain 1 to 50% by weight hesperetin and/or the salts thereof, based on the total weight of the preparation, 0 to 10% by weight of other flavours, based on the total weight of the preparation, 50 to 99% by weight carriers, based on the total weight of the preparation, and 0 to 50% by weight of further auxiliaries and/or stabilisers, based on the total weight of the preparation.

The spray-dried, solid preparations according to the invention are particularly suitable as semi-finished products for producing further preparations according to the invention as the solubility of the hesperetin and/or the salts thereof to be used according to the invention is significantly improved by the carriers and/or auxiliaries, in particular by maltodextrin, starch, natural or synthetic polysaccharides and/or plant gums, such as modified starches or gum arabic. The spray-dried, solid preparations according to the invention preferably contain 50 to 95% % by weight carriers, in particular maltodextrin and/or starch, 5 to 40% auxiliaries, preferably natural or synthetic polysaccharides and/or plant gums, such as modified starches or gum Arabic, and 1 to 45% hesperetin and/or the salts thereof.

According to a further preferred embodiment the hesperetin and/or the salts thereof to be used according to the invention and optionally other constituents of the preparation according to the invention are incorporated firstly into emulsions, liposomes, e.g. starting from phosphatidylcholine, microspheres, nanospheres or in capsules, granules or extrudates of a matrix suitable for foods and semi-luxury foods, e.g. of starch, starch derivates (e.g. modified starch), cellulose or cellulose derivates (e.g. hydroxypropyl cellulose), other polysaccharides (e.g. dextrin, alginate, curdlan, carrageenan, chitin, chitosan, pullulan), natural fats, natural waxes (e.g. beeswax, carnauba wax), of proteins, e.g. gelatines or other natural products (e.g. shellac), to produce preparations according to the invention. Depending on the matrix the products may also be obtained by spray drying, spray granulation, melt granulation, coacervation, coagulation, extrusion, melt extrusion, emulsion processes, coating or other suitable encapsulation processes and optionally a suitable combination of said processes. In a further preferred production process for a preparation according to the invention the hesperetin and/or the salts thereof is/are firstly complexed with one or more suitable complexing agent(s), for example with cyclodextrins or cyclodextrin derivates, preferably α- or β-cyclodextrin, and used in this complexed form.

Particularly preferred is a preparation according to the invention in which the matrix is selected such that the hesperetin and/or the salts thereof is/are liberated from the matrix with a delay, so a long-lasting effect is achieved. Particularly preferred is a fat, wax, polysaccharide or protein matrix in this regard.

As further constituents for preparations according to the invention used for nourishment or consumption, conventional raw materials, auxiliaries and additives for foods or semi-luxury foods can be used, e.g. water, mixtures of fresh or processed, vegetable or animal basic or raw materials (e.g. raw, roasted, dried, fermented, smoked and/or cooked meat, bones, cartilage, fish, vegetables, fruits, herbs, nuts, vegetable or fruit juices or pastes or mixtures thereof), digestible or non-digestible carbohydrates (e.g. saccharose, maltose, fructose, glucose, dextrins, amylose, amylopectin, inulin, xylanes, cellulose, tagatose), sugar alcohols (e.g. sorbitol, erythritol), natural or hardened fats (e.g. tallow, lard, palm butter, coconut oil, hydrogenated vegetable fat), oils (e.g. sunflower oil, groundnut oil, maize oil, olive oil, fish oil, soya oil, sesame oil), fatty acids or the salts thereof (e.g. potassium stearate), proteinogenic or non-proteinogenic amino acids and related compounds (e.g. γ-aminobutyric acid, taurine), peptides (e.g. gluthathion), natural or processed proteins (e.g. gelatines), enzymes (e.g. peptidases), nucleic acids, nucleotides, taste corrigents for unpleasant taste impressions, further taste modulators for further, generally not unpleasant taste impressions, other taste-modulating substances (e.g. inositolphosphate, nucleotides, such as guanosinmonophosphate, adenosinmonophosphate or other substances, such as sodium glutamate or 2-phenoxypropionic acid), emulsifiers (e.g. lecithins, diacylglycerols, gum arabic), stabilisers (e.g. carrageenan, alginate), preservatives (e.g. benzoic acid, sorbinic acid), antioxidants (e.g. tocopherol, ascorbic acid), chelators (e.g. citric acid), organic or inorganic acids (e.g. malic acid, acetic acid, citric acid, tartaric acid, phosphoric acid), bitter principles (e.g. quinine, caffeine, limonine, amarogentine, humolone, lupolone, catechins, tannins), mineral salts (e.g. sodium chloride, potassium chloride, magnesium chloride, sodium phosphates), substances preventing enzymatic browning (e.g. sulphite, ascorbic acid), etheric oils, plant extracts, natural or synthetic colourings or colouring pigments (e.g. carotinoids, flavonoids, anthocyans, chlorophyll and the derivates thereof), spices, trigeminally active substances or plant extracts containing such trigeminally active substances, synthetic, natural or nature-identical flavourings or perfumes and odour corrigents.

Dental care products (as a basis for preparations used for oral hygiene) which contain the hesperetin and/or the salts thereof to be used according to the invention generally comprise an abrasive system (abrasive or polish), such as e.g. silicic acids, calcium carbonates, calcium phosphates, aluminium oxides and/or hydroxylapatites, surface-active substances, such as e.g. sodium laurylsulphate, sodium lauryl sarcosinate and/or cocamidopropyl betaine, humectants, such as e.g. glycerol and/or sorbitol, thickeners, such as e.g. carboxymethyl cellulose, polyethylene glycols, carrageenan and/or Laponite®, sweeteners, such as e.g. saccharin, taste corrigents for unpleasant taste impressions, taste corrigents for further, generally not unpleasant taste impressions, taste-modulating substances (e.g. inositolphosphate, nucleotides such as guanosinmonophosphate, adenosinmonophosphate or other substances such as sodium glutamate or 2-phenoxypropionic acid), cooling active ingredients, such as e.g. menthol, menthol derivatives (e.g. L-menthol, L-menthyl lactate, L-menthyl alkyl carbonates, menthone ketals, menthanecarbonic acid amides), 2,2,2-trialkylacetic acid amides (e.g. 2,2-diisopropylpropionic acid methylamide), icilin and icilin derivatives, stabilisers and active ingredients, such as e.g. sodium fluoride, sodium monofluorophosphate, tin difluoride, quaternary ammonium fluorides, zinc citrate, zinc sulphate, tin pyrophosphate, tin dichloride, mixtures of various pyrophosphates, triclosan, cetylpyridinium chloride, aluminium lactate, potassium citrate, potassium nitrate, potassium chloride, strontium chloride, hydrogen peroxide, flavours and/or sodium bicarbonate or odour corrigents.

Chewing gums (as a further example of preparations used for oral hygiene), which contain the hesperetin and/or the salts thereof to be used according to the invention generally comprise a chewing gum base, i.e. a chewing compound that plasticises on chewing, various types of sugar, sugar substitutes, other sweet-tasting substances, sugar alcohols, taste corrigents for unpleasant taste impressions, other taste modulators for further, generally not unpleasant taste impressions, taste-modulating substances (e.g. inositolphosphate, nucleotides such as guanosinmonophosphate, adenosinmonophosphate or other substances such as sodium glutamate or 2-phenoxypropionic acid), humectants, thickeners, emulsifiers, flavours and stabilisers or odour corrigents.

The preparations according to the invention can preferably also contain a flavour composition to round off and refine the taste and/or odour of the preparation. Suitable flavour compositions contain e.g. synthetic, natural or nature-identical flavourings, perfumes and flavours and suitable auxiliaries and carriers. Particularly preferred are preparations according to the invention which contain one or more flavouring(s) which give(s) a "sweet" olfactory impression (see above in this regard).

Preparations according to the invention which are in the form of semi-finished products can be used to enhance the sweet taste impression of ready-to-use preparations which are produced using the semi-finished product preparation.

In a particularly preferred embodiment of the invention the hesperetin and/or the salts thereof to be used according to the invention are used in the preparations according to the invention in combination with at least one (further) substance capable of masking or reducing an unpleasant (bitter, chalky, acidic, astringent) taste impression or for enhancing a pleasant taste impression (sweet, salty, savory). A particularly effective enhancement of the sweetness may thus be achieved, for example. The combination of the hesperetin or salts thereof to be used according to the invention with taste corrigents for unpleasant, in particular bitter, taste impressions or flavour enhancers for pleasant, in particular sweet, taste impressions is preferred in particular.

The (further) taste corrigents are selected for example from the following list: nucleotides (e.g. adenosin-5'-monophosphate, cytidin-5'-monophosphate) or the pharmaceutically acceptable salts thereof, lactisoles, sodium salts (e.g. sodium chloride, sodium lactate, sodium citrate, sodium acetate, sodium gluconate), further hydroxyflavanones (e.g. eriodictyol, homoeriodictyol or the sodium salts thereof), in particular according to US 2002 188,019, hydroxybenzoic acid amides (e.g. 2,4-dihydroxybenzoic acid vanillylamide, 2,4-dihydroxybenzoic acid-N-(4-hydroxy-3-methoxybenzyl)amide, 2,4,6-trihydroxybenzoic acid-N-(4-hydroxy-3-methoxybenzyl)amide, 2-hydroxy-benzoic acid-N-4-(hydroxy-3-methoxybenzyl)amide, 4-hydroxybenzoic acid-N-(4-hydroxy-3-methoxybenzyl)amide, 2,4-dihydroxybenzoic acid-N-(4-hydroxy-3-methoxybenzyl)amide-mono-sodium salt, 2,4-dihydroxybenzoic acid-N-2-(4-hydroxy-3-methoxyphenyl)ethylamide, 2,4-dihydroxybenzoic acid-N-(4-hydroxy-3-ethoxybenzyl)amide, 2,4-dihydroxybenzoic acid-N-(3,4-dihydroxybenzyl)amide and 2-hydroxy-5-methoxy-N-[2-(4-hydroxy-3-methoxyphenyl)ethyl]amide (aduncamide), 4-hydroxybenzoic acid vanillylamide), hydroxydeoxybenzoins (e.g. 2-(4-hydroxy-3-methoxyphenyl)-1-(2,4,6-trihydroxyphenyl)ethanone, 1-(2,4-dihydroxyphenyl)-2-(4-hydroxy-3-methoxyphenyl)ethanone, 1-(2-hydroxy-4-methoxyphenyl)-2-(4-hydroxy-3-methoxyphenyl)ethanone), amino acids (e.g. gamma-aminobutyric acid) or mixtures of whey proteins with lecithins.

The present invention also relates to a process for enhancing the sweet taste of a sweet-tasting substance or the sweet olfactory impression of a flavouring which gives a sweet olfactory impression, comprising the following step:

mixing a sweet-tasting substance or a flavouring which gives a sweet olfactory impression with a quantity of (i) hesperetin and/or (ii) the salts thereof which is sufficient to enhance in sensory terms the sweet taste impression of the sweet-tasting substance(s) or the sweet olfactory impression of the flavouring(s) which give(s) a sweet olfactory impression.

See above for preferred quantities of (i) hesperitin or (ii) the salts thereof. A concentration of at least 10 ppm is often particularly preferred.

The hesperetin and/or the salts thereof are preferably not (a) in the form of an exudate of a sclerophyllous evergreen plant, in particular *Artemisia xanthochroa* or *Chysothamnus* ssp., and not (b) used together with other flavanones as a constituent of the same citrus product either in the process according to the invention.

EXAMPLES

The examples are used to clarify the invention, without restricting it thereby.

Application Example 1

Enhancing the Sweet Impression of a Sugar Solution by Adding Hesperetin

In order to quantify the enhancement of a sweet impression owing to the addition of hesperetin, the respective sweetness of a 5% by weight sucrose-containing solution and of samples which contained 5% sucrose and 100 ppm hesperetin (source: Sigma-Aldrich, Order.-No. H 4125, CA-No. 41001-90-5) or a quantity of comparative hydroxyflavanones naringenin, eriodictyol, homoeriodictyol or eriodictyol-7-methylether (cf. US 2002 188,019) was determined by a group of experts (rating 0 [not sweet] to 10 [extremely sweet]). Evaluation took place as a calculation of the enhancement (in %) of the sweet impression from the mean values of the assessments of the sucrose solution or the sucrose and compound 2-containing solution.

TABLE

| Substance (per 100 ppm) | Sweet impression (1-10) a) without | Sweet impression (1-10) b) with | % Enhancement of the sweet impression |
|---|---|---|---|
| Hesperetin (according to the invention) | 5.0 ± 1.9 | 7.1 ± 2.4 | +41% (16/14) significant, p < 0.05 |
| Naringenin (comparison) | 5.6 ± 1.6 | 6.0 ± 1.7 | +7.5% (19/12) |
| Eriodictyol (comparison) | 6.5 ± 1.2 | 5.4 ± 1.2 | −16.7% (12/2) significant, p < 0.05 |
| Homoeriodictyol (comparison) | 5.7 ± 1.8 | 6.1 ± 1.5 | +6.4% (19/13) |
| Eriodictyol-7-methylether (comparison) | 4.9 ± 1.2 | 5.7 ± 1.9 | +15.9 (18/13) | sweetness of (a) a sucrose solution and (b) a sucrose and a hydroxyflavanone-containing solution; the standard deviations are given as an error. The last column indicates in brackets the total number of tasters against the number of tasters who found the test solution sweeter.

Application Example 2

Sweet Impression of a Sugar-Reduced Test Solution

In order to quantify the retention of a sweet impression when replacing a sucrose content with a small quantity of hesperetin, the respective sweetness of (a) a 6% by weight sucrose-containing solution against a 5% by weight sucrose-containing solution and (b) a 6% by weight sucrose-containing solution against a solution which contained 5% sucrose and a quantity of hesperetin (source: Sigma-Aldrich, Order No. H 4125, CA-No. 41001-90-5) was determined by a group of experts (rating 0 [not sweet] to 10 [extremely sweet]). Evaluation took place as a calculation of the enhancement (in %) of the sweet impression from the mean values of the assessments of the 6% or 5% sucrose-containing solution or 5% sucrose and 100 ppm hesperetin-containing solution.

TABLE

| Test | Sweet impression (1-10) | | % Enhancement of the sweet impression |
|---|---|---|---|
| | 6% sucrose | 5% sucrose | |
| (a) | 6.9 ± 1.6 | 5.0 ± 1.6 | −30% (15/0) |
| | 6% sucrose | 5% sucrose + 100 ppm hesperetin | |
| (b) | 6.5 ± 1.5 | 7.9 ± 1.5 | +21% (15/12) |

Sweetness (a) of a 6% by weight sucrose solution against a 5% by weight sucrose solution, (b) of a 6% by weight sucrose-containing against a 5% by weight sucrose and 100 ppm hesperetin-containing solution; standard deviations are given as errors. The last column indicates in brackets the total number of tasters against the number of tasters who found the test solution containing 5% sucrose and optionally 100 ppm hesperetin sweeter.

Application Example 3

Spray-Dried Preparation as a Semi-Finished Product for Flavouring Finished Goods

| Ingredient | Use in % by weight |
|---|---|
| Drinking water | 60.8% |
| Maltodextrin from wheat | 24.3% |
| Gum arabic | 6.1% |
| Hesperetin | 8.8% |

The drinking water was placed in a container and the maltodextrin and gum arabic dissolved therein. Hesperetin was then emulsified in the carrier solution using a Turrax. The temperature of the spray solution should not exceed 30° C. The mixture was then spray dried (desired temperature at inlet: 185-195° C., desired temperature at outlet: 70-75° C.). The spray dried semi-finished product contained ca 18-22% hesperetin.

Application Example 4

Combination with Sweet-Tasting Substances 90 g sucrose and 10 g tagatose were compounded and mixed with 0.5 g of the spray-dried semi-finished product from Application Example 3. The resulting product can be used e.g. as a sweetener for coffee or tea.

The tea and the product were mixed and packed in teabags made of filter paper. For use, 100-250 ml boiling water was poured onto a teabag and allowed to draw for 2-5 min.

Application Example 5

Use in a Low-Fat Yoghurt for Enhancing the Sweetness

5% sucrose was stirred into a commercially available natural yoghurt (without additives) with a 0.1% fat content (sample 1). 5% sucrose and also 200 ppm hesperetin were stirred into a sample 2. The samples 1 and 2 were presented to 16 tasters in coded form for tasting in different but predetermined orders. In the process the tasters had to grade the sweet impression on a scale from 0 (non-existent) to 10 (extremely sweet). In addition, the tasters were to grade other taste impressions.

Result: sample 2 was, on average, described as 15% sweeter.

Application Example 6

Use in a Chewing Gum

| Part | Ingredient | Use in % by weight |
|---|---|---|
| A | Chewing gum base, Company "Jagum T" | 30.00 |
| B | Sorbitol, pulverised | 39.00 |
| | Isomalt ® (Palatinit GmbH) | 9.50 |
| | Xylitol | 2.00 |
| | Mannitol | 3.00 |
| | Aspartame ® | 0.10 |
| | Acesulfame ® K | 0.10 |
| | Emulgum ® (Colloides Naturels, Inc.) | 0.30 |

-continued

| Part | Ingredient | Use in % by weight |
| --- | --- | --- |
| C | Sorbitol, 70% | 14.00 |
|  | Glycerol | 1.00 |
| D | Flavour, containing 1% by weight hesperetin, based on the total weight of the flavour | 1 |

Parts A to D were mixed and intensively kneaded. The raw mixture can be processed, e.g. in the form of thin strips, into ready-to-consume chewing gums.

Application Example 7

Use in a Toothpaste

| Part | Ingredient | Use in % by weight |
| --- | --- | --- |
| A | Demineralised water | 22.00 |
|  | Sorbitol (70%) | 45.00 |
|  | Solbrol ® M, sodium salt (Bayer AG, p-hydroxybenzoic acid alkylester) | 0.15 |
|  | Trisodium phosphate | 0.10 |
|  | Saccharin, 450-fold | 0.20 |
|  | Sodium monofluorophosphate | 1.12 |
|  | Polyethylene glycol 1500 | 5.00 |
| B | Sident 9 (abrasive silicon dioxide) | 10.00 |
|  | Sident 22 S (thickening silicon dioxide) | 8.00 |
|  | Sodium carboxymethylcellulose | 0.90 |
|  | Titanium dioxide | 0.50 |
| C | Demineralised water | 4.53 |
|  | Sodium laurylsulphate | 1.50 |
| D | Flavour, containing 1% by weight hesperetin, based on the total weight of the flavour | 1 |

The ingredients of parts A and B were each pre-mixed on their own and thoroughly stirred together under vacuum at 25-30° C. for 30 min. Part C was premixed and added to A and B; D was added and the mixture thoroughly stirred under vacuum at 25-30° C. for 30 min. Following relaxation the toothpaste was finished and could be decanted into containers.

Application Example 8

Use in a Sugar-Reduced Soft Drink

Comparative preparation with normal sucrose content (A)

Comparative preparation with reduced sucrose content (B)

Preparation with reduced sucrose content and hesperetin (C)

|  | Content | | |
| --- | --- | --- | --- |
| Ingredient | Preparation A | Preparation B | Preparation C |
| Water | 89.85% | 91.85% | 91.85% |
| Sucrose | 10.0% | 8.0% | 8.0% |
| Citric acid | 0.15% | 0.2% | 0.2% |
| Hesperetin | — | — | 0.01% |

The solid substances were placed in a container and topped up with water and dissolved. The tasting results are listed in the following Table:

| Preparation | Sweet impression (1-10) | Enhancement/reduction |
| --- | --- | --- |
| A (normal sucrose content) | 5.8 ± 1.7 | — |
| B (reduced sucrose content) | 4.0 ± 1.5 | B against A: −31% |
| C (reduced sucrose content + 100 ppm hesperetin) | 5.3 ± 1.8 | C against A: −11% C against B: +33% |

With preparation C, which also had a higher acid content, the sweetness of the 10% sucrose-containing comparative preparation A was almost attained; the slight reduction in sweetness of 11% is statistically insignificant.

A significantly more pronounced sweetness was perceptible even for preparation C compared with comparative preparation B.

Application Example 9

Use in a Sugar-Free Hard Boiled Candy

| Ingredient | Content (%) |
| --- | --- |
| Palatinite, Type M | 75.10% |
| Water | 24.82% |
| Peppermint flavour | 0.1% |
| Hesperetin | 0.01% |

Palatinite was mixed with water and the mixture melted at 165° C. and then allowed to cool to 115° C. The peppermint flavour and hesperetin were added and after thorough mixing the mixture was poured into moulds and allowed to harden therein.

Application Example 10

Use in a Sugar-Reduced Hot Blancmange-Type Pudding

Comparative preparation with normal sucrose content (A)

Comparative preparation with reduced sucrose content (B)

Preparation with reduced sucrose content and hesperetin (C)

Preparation with reduced sucrose content, D-tagatose and hesperetin (D)

| Ingredient | Content in % by weight | | | |
|---|---|---|---|---|
| | Preparation A | Preparation B | Preparation C | Preparation D |
| Sucrose | 7.8% | 5.4% | 5.4% | 5.4% |
| Starch | 3.0% | 3.0% | 3.0% | 3.0% |
| Skimmed milk powder | 1.5% | 1.5% | 1.5% | 1.5% |
| Aubygel MR50 | 0.5% | 0.5% | 0.5% | 0.5% |
| Vanilla q.v., Symrise #655064 | 0.1% | 0.1% | 0.1% | 0.1% |
| Hesperetin | — | — | 0.02% | 0.01% |
| D-tagatose | — | — | — | 0.1% |
| Milk 1.5% fat content | Top up to 100% | Top up to 100% | Top up to 100% | Top up to 100% |

The solid substances were placed in a container and stirred together with the milk. The mixture was heated to 95° C. for 2 min while stirring thoroughly, decanted into containers and cooled to 5-8° C.

With preparation C the sweetness of the 7.8% sucrose-containing comparative preparation A could be achieved with a slightly delayed sweetness impression. Compared with comparative preparation B, preparation C was significantly sweeter. Preparation D was comparable with C, but exhibited improved initial sweetness.

Application Example 11

Use Together with Sweeteners in Low-Fat Yoghurt

Comparative preparation with sweetener mixture (A)
Preparation with sweetener mixture and hesperetin (B)

| Ingredient | Content (in % by weight) | |
|---|---|---|
| | Preparation A | Preparation B |
| D-tagatose | 0.482% | 0.482% |
| Sucralose | 0.003% | 0.003% |
| Aspartame | 0.005% | 0.005% |
| Acesulfame K | 0.01% | 0.01% |
| Hesperetin | — | 0.01% |
| Yoghurt, 0.1% fat | Top up to 100% | Top up to 100% |

The ingredients were mixed and cooled at 5° C. The sweetness of preparation B was described as significantly more intense during tasting.

Preferred embodiments of the invention follow:

Embodiments of the Invention

1. Use of
(i) hesperetin of formula (I)

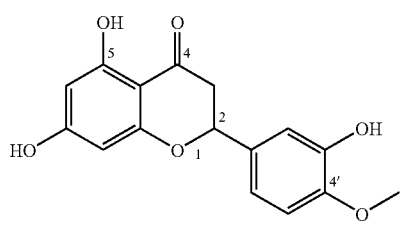

(I)

wherein the hesperetin of formula (I) is in the form of a (2S)-enantiomer, (2R)-enantiomer or any desired mixture of the two enantiomers,
and/or
(ii) the salts thereof
for enhancing the sweet taste of a sweet-tasting substance or the sweet olfactory impression of a flavouring which gives a sweet olfactory impression.

2. Use according to embodiment 1, for enhancing the sweet taste of a sweet-tasting substance or the sweet olfactory impression of a flavouring which gives a sweet olfactory impression, in a preparation used for nourishment, oral hygiene or consumption.

3. Use according to embodiment 1 or 2, for enhancing the sweet taste of a sweet-tasting substance or the sweet olfactory impression of a flavouring which gives a sweet olfactory impression, in ready-to-consume foods and semi-luxury foods, wherein the concentration (i) of the hesperetin and/or (ii) the salts thereof is less than 0.025% by weight, preferably less than 0.02% by weight, based on the total weight of ready-to-consume foods and semi-luxury foods.

4. The preparation used for nourishment, oral hygiene or consumption, comprising
(i) hesperetin of formula (I)

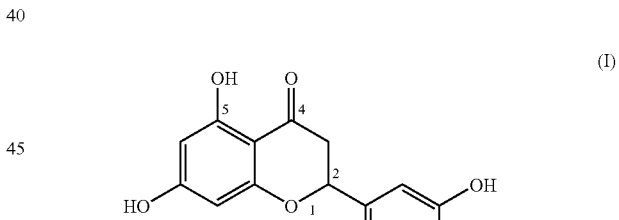

(I)

wherein the hesperetin of formula (I) is in the form of a (2S)-enantiomer, (2R)-enantiomer or any desired mixture of the two enantiomers,
and/or
(ii) the salts thereof
and
one or more further (iii) sweet-tasting substance(s) and/or (iv) flavouring(s) which give(s) a sweet olfactory impression,
wherein the quantity of (i) hesperetin and (ii) the salts thereof in the preparation is sufficient to enhance in sensory terms the sweet taste impression of the sweet-tasting substance(s) or the sweet olfactory impression of the flavouring(s) which give(s) a sweet olfactory impression.

5. Preparation according to embodiment 4, comprising as a sweet-tasting substance or sweet-tasting substances one or more sugar(s), wherein the quantity of (i) hesperitin or (ii) the salts thereof is sufficient to impart the same or an enhanced sweetness impression compared with a preparation which, with an otherwise identical composition, contains neither hesperitin nor the salts thereof, but at least 1.05 times the quantity of sugar.

6. Preparation according to embodiment 4 or 5, wherein the hesperetin and/or the salts thereof is/are not used (a) in the form of an exudate of a sclerophyllous evergreen plant, in particular *Artemisia xanthochroa* or *Chysothamnus* ssp., or (b) together with other flavanones as a constituent of the same citrus product.

7. Preparation according to any one of embodiments 4 to 6, characterised in that it is in the form of a semi-finished product, a perfume, flavouring or flavour composition or spice mixture.

8. Semi-finished product according to embodiment 7, characterised in that it is spray-dried.

9. Preparation according to any one of embodiments 7 or 8, comprising in total 0.0001% by weight to 95% by weight, preferably 0.001% by weight to 80% by weight, particularly preferably 0.001% by weight to 50% by weight, based on the total weight of the preparation of (i) hesperetin and (ii) the salts thereof.

10. Preparation according to any one of embodiments 4 to 9, also comprising at least one further substance for masking or reducing a bitter, metallic, chalky, acidic or astringent taste impression or for enhancing a sweet, salty or savoury taste impression.

11. Process for enhancing the sweet taste of a sweet-tasting substance or the sweet olfactory impression of a flavouring which gives a sweet olfactory impression, comprising the following step:
    mixing a sweet-tasting substance or a flavouring which gives a sweet olfactory impression with a quantity of (i) hesperetin and/or (ii) the salts thereof which is sufficient to enhance in sensory terms the sweet taste impression of the sweet-tasting substance(s) or the sweet olfactory impression of the flavouring(s) which give(s) a sweet olfactory impression.

12. Process according to embodiment 11, wherein the hesperetin and/or the salts thereof is/are not used (a) in the form an exudate of a sclerophyllous evergreen plant, in particular *Artemisia xanthochroa* or *Chysothamnus* ssp., or (b) together with other flavanones as a constituent of the same citrus product.

PART B

Description of Invention Following Further Development

The invention primarily relates to the use of hesperetin and/or the salts thereof for enhancing the sweet taste of sweet-tasting substances or the sweet olfactory impression of flavourings which give a sweet olfactory impression. The invention thus primarily relates to the use of said substances as sweetness enhancers. The invention also relates to specific preparations containing an effective content of hesperetin and/or the salts thereof and to processes for enhancing the sweet taste of a sweet-tasting substance or the sweet olfactory impression of a flavouring which gives a sweet olfactory impression.

Foods (nourishment, including beverages) or semi-luxury foods (semi-luxuries) that have a high sugar content (primarily sucrose (=saccharose), lactose, glucose or fructose or mixtures thereof) are usually strongly preferred by consumers owing to their sweetness. On the other hand it is generally known that a high content of easily metabolisable carbohydrates allows the blood sugar level to greatly increase, leads to the formation of fatty deposits and can ultimately lead to health problems, such as excess weight, obesity, insulin resistance, late-onset diabetes and their secondary diseases. In particular there is also the aggravation that many of the above-mentioned carbohydrates can also affect dental health as they are broken down by specific types of bacteria in the oral cavity into lactic acid for example and can attack the tooth enamel of adolescent or adult teeth (cavities).

It has therefore long been an aim to reduce the sugar content of foods and/or semi-luxury foods to the absolutely necessary amount. A corresponding measure consists in the use of sweeteners. These are chemically uniform substances which do not themselves have a calorific value, or have only a very low calorific value, and simultaneously give a strong sweet taste impression. The substances are usually non-cariogenic (an overview can be found for example in: Journal of the American Dietetic Association 2004, 104 (2), 255-275). Some of what are known as bulk sweeteners, such as sorbitol, mannitol or other sugar alcohols, are outstanding sweeteners and can also partially replace the remaining food technology-related properties of sugars, but too frequent intake leads to osmotically-induced digestion problems among some people. While, owing to their low concentration in use, the non-nutritive, highly intensive sweeteners are very suitable for bringing sweetness into foods, they often exhibit taste-related problems as a result of time-intensity profiles which are not similar to sugar (e.g. sucralose, stevioside, cyclamate), a bitter and/or astringent aftertaste (e.g. acesulfame K, saccharin), or pronounced additional taste impressions (e.g. glycyrrhetinic acid ammonium salt). Some of the sweeteners are not particularly stable as regards heat (e.g. thaumatin, brazzein, monellin), are not stable in all applications (e.g. aspartame) and are sometimes very long-lasting in terms of their sweet effect (strong sweet aftertaste, e.g. saccharin).

An improvement in the taste properties, in particular the aftertaste problem of non-nutritive, highly intensive sweeteners can be achieved by the use of tannic acid, e.g. as described in WO 98/20753, or phenolic acids as in U.S. Pat. No. 3,924, 017. However, substances of this type are not particularly stable in applications owing to their catechol units.

A further possibility—without using non-nutritive sweeteners—consists in reducing the sugar content of foods and/or semi-luxury foods and adding sensorily weak or imperceptible substances which indirectly or directly enhance the sweetness, as are described for example in WO 2005/041684. The substances described in WO 2005/041684 are, however, explicitly of non-natural origin and are therefore more difficult to assess from a toxicological perspective than substances of natural origin, in particular if the latter occur in foods or semi-luxury foods or originate from raw materials for obtaining foods or semi-luxury foods. EP 1 291 342 A1 describes such substances of natural origin (pyridinium betaines). However, they do not selectively affect the sweet taste, rather other tastes, such as savouriness or saltiness, are affected. In addition, the disclosed substances can only be purified with high expenditure.

It is therefore desirable to find substances which in low concentrations effectively enhance the sweet taste impressions of sweet substances, preferably the sweet taste impression of reduced-sugar foods and semi-luxury foods, without adversely affecting the remaining flavour profile. It is also desirable to find substances which in low concentrations effectively enhance sweet impressions of flavourings which give a sweet olfactory impression.

Further relevant documents are U.S. Pat. No. 5,580,545, U.S. Pat. No. 5,703,053, WO 2005/006891, EP 1 258 200, EP 0 577 143, EP 0 691 886, EP 0 920 870, EP 0 960 572, EP 1 072 265, EP 1 127 572, EP 1 177 728, EP 1 283 037, EP 1 382 329, EP 1 400 579, EP 1 514 540, EP 1 534 082, US 2001055627, US 2003166584, U.S. Pat. No. 5,763,414, U.S. Pat. No. 6,221,357, U.S. Pat. No. 6,426,362, U.S. Pat. No. 6,528,042, U.S. Pat. No. 6,749,875, WO 00/15174, WO 00/23073, WO 00/64282, WO 01/14396, WO 01/17374, WO 02/34073, WO 02/47615, WO 02/47680, WO 03/039452, WO 03/043570, WO 2004/002496, WO 2004/021806, WO 2004/100981, WO 2005/058255, WO 2005/067915, WO 91/11117, WO 99/21549, WO 99/48982, WO 99/62358, WO 01/51482 and JP 62051613.

The primary object of the present invention was to find substances which (a) are selectively suitable for enhancing the sweet taste of a sweet-tasting substance and/or the sweet olfactory impression of a flavouring which gives a sweet olfactory impression, preferably without adversely affecting the remaining flavour profile, (b) can be widely used and (c) preferably occur naturally, preferably in foods or semi-luxury foods or the corresponding raw materials for the preparation thereof or are formed during the production of foods or semi-luxury foods.

According to a first aspect of the present invention the object posed is achieved by the use of hesperetin of formula (I)

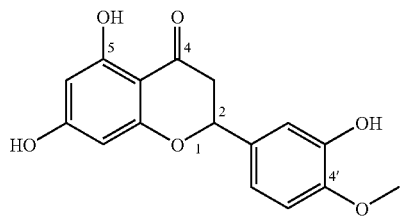

(I)

wherein the hesperetin of formula (I) is in the form of a (2S)-enantiomer, (2R)-enantiomer or any desired mixture of the two enantiomers,
a salt of hesperetin of formula (I),
a mixture comprising or consisting of two or more salts of the hesperetin of formula (I),
or
a mixture comprising or consisting of
hesperetin of formula (I), and one or more salt(s) of hesperetin of formula (I)
for enhancing the sweet taste of a sweet-tasting substance or the sweet olfactory impression of a flavouring which gives a sweet olfactory impression.

With a use of this type according to the invention the total of the substance amount fractions of (2S)-enantiomer of hesperetin of formula (I) and the salts thereof is preferably greater than or equal to 50%, preferably greater than or equal to 80%, and particularly preferably 100%, based on the total of the substance amount fractions of the (2S)-enantiomer of hesperetin of formula (I), the (2R)-enantiomer of hesperetin of formula (I) and the salts thereof.

In salts of the hesperetin of the above formula (I) to be used according to the invention one, a plurality of or all group(s) of the hesperetin that can be deprotonated are deprotonated. There is then an appropriate quantity of counterions, wherein these are preferably selected from the group comprising: singly positively charged cations of the first primary and secondary group, ammonium ions, trialkylammonium ions, doubly positively charged cations of the second primary and secondary group and trebly positively charged cations of the third primary and secondary group and mixtures thereof.

Particularly preferred cations are $Na^+$, $K^+$, $NH_4^+$, $Ca^{2+}$, $Mg^{2+}$, $Al^{3+}$ and $Zn^{2+}$.

The above-mentioned substances and substance mixtures to be used according to the invention are preferably used for enhancing the sweet taste of a sweet-tasting substance or the sweet olfactory impression of a flavouring which gives a sweet olfactory impression, in a preparation used for nourishment, oral hygiene or consumption.

In addition to the use of specific substances or substance mixtures previously mentioned, according to a further aspect the invention also relates to corresponding preparations in which said substances or substance mixtures are used in the manner according to the invention.

A preparation according to the invention is preferably selected from the group comprising preparations used for nourishment, oral hygiene or consumption, semi-finished products, perfume, flavouring or flavour compositions or spice mixtures. A preparation according to the invention comprises the following components:

(a)
hesperetin of formula (I)

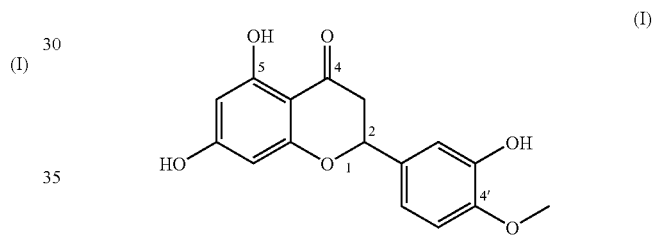

(I)

wherein
the hesperetin of formula (I) is in the form of a (2S)-enantiomer, (2R)-enantiomer or any desired mixture of the two enantiomers,
a salt of hesperetin of formula (I),
a mixture comprising or consisting of two or more salts of the hesperetin of formula (I),
or
a mixture comprising or consisting of
hesperetin of formula (I), and one or more salt(s) of hesperetin of formula (I),
and
(b) one or more further sweet-tasting substance(s)
and/or
(c) one or more flavouring(s) which give(s) a sweet olfactory impression,
wherein the total quantity of component (a) in the preparation is sufficient to enhance, preferably superproportionally (i.e. beyond an effect caused by the inherent sweetness), in sensory terms the sweet taste impression of the sweet-tasting substance(s) (b) or the sweet olfactory impression of the flavouring(s) (c) which give(s) a sweet olfactory impression.

In a preparation according to the invention the total of the substance amount fractions of the (2S)-enantiomer of the hesperetin of formula (I) and the salts thereof is preferably greater than or equal to 50%, preferably greater than or equal to 80%, and particularly preferably 100%, based on the total of the substance amount fractions of the (2S)-enantiomer of the hesperetin of formula (I), the (2R)-enantiomer of the hesperetin of formula (I) and the salts thereof.

It should be noted at this point that all statements relating to preferred embodiments of a use according to the invention, a preparation according to the invention or a process according to the invention apply in each case to the other aspects of the invention accordingly.

A preferred preparation according to the invention comprises as component (b) one or more sugar(s), wherein the total quantity of (i) hesperetin of formula (I) and (ii) the salts thereof (component (a)) in the preparation is sufficient to impart the same or an enhanced sweetness impression compared with a preparation or semi-finished product which, with an otherwise identical composition, comprises neither (i) hesperetin of formula (I) nor (ii) the salts thereof, but at least 1.05 times the quantity (preferably at least 1.2 times, preferably 1.4 times the quantity) of sugar(s). The sugars are preferably selected from the group comprising: sucrose, lactose, glucose, fructose and mixtures thereof.

The hesperetin to be used according to the invention (or the salts thereof and mixtures) may be of natural origin (for example from plant part extracts). The substances or substance mixtures to be used according to the invention may also be purely synthetic, however.

A preferred preparation according to the invention (as described above, in particular in a preferred embodiments) comprises
(b) one or more further sweet-tasting substance(s), wherein the further sweet-tasting substance(s) is/are selected from the group comprising:
(i) one or more carbohydrates (sugars) selected from the group comprising sucrose, trehalose, lactose, maltose, melizitose, melibiose, raffinose, palatinose, lactulose, D-fructose, D-glucose, D-galactose, L-rhamnose, D-sorbose, D-mannose, D-tagatose, D-arabinose, L-arabinose, D-ribose, D-glyceraldehyde, maltodextrin and vegetable preparations containing one or more of said carbohydrate(s), (preferably in a content of at least 5% by weight, preferably at least 15% by weight), wherein these carbohydrates may also be in the form of a natural or synthetically produced mixture (e.g. as a honey, invert sugar syrup, highly enriched fructose syrups made from corn starch [high fructose corn syrup])
(ii) one or more sugar alcohol(s) selected from the group comprising glycerol, erythritol, threitol, arabitol, ribitol, xylitol, sorbitol, mannitol, dulcitol and lactitol,
(iii) one or more protein(s) and/or amino acids from the group comprising miraculin, monellin, thaumatin, curculin, brazzein, glycine, D-leucine, D-threonine, D-asparagine, D-phenylalanine, D-tryptophan, L-proline,
(iv) one or more sweetener(s) from the group comprising magap, sodium cyclamate, acesulfame K, neohesperidin dihydrochalcone, saccharin sodium salt, aspartame, superaspartame, neotam, alitame, sucralose, stevioside, rebaudioside, lugduname, carrelame, sucrononate, sucrooctate, monatin and phyllodulcin,
and the mixtures thereof
and/or
(c) one or more flavouring(s) which give(s) a sweet olfactory impression, wherein the further flavouring(s) which give(s) a sweet olfactory impression are selected from the group comprising: vanillin, ethylvanillin, ethylvanillin isobutyrate (=3-ethoxy-4-isobutyryloxybenz-aldehyde), Furaneol® (2,5-dimethyl-4-hydroxy-3(2H)-furanone) and derivatives (e.g. homofuraneol, 2-ethyl-4-hydroxy-5-methyl-3(2H)-furanone), homofuranol (2-ethyl-5-methyl-4-hydroxy-3(2H)-furanone and 5-ethyl-2-methyl-4-hydroxy-3(2H)-furanone), maltol and derivatives (e.g. ethylmaltol), coumarin and derivatives, gamma-lactones (e.g. gamma-undecalactone, gamma-nonalactone), delta-lactones (e.g. 4-methyldeltalactone, massoilactone, deltadecalactone, tuberolactone), methyl sorbate, divanillin, 4-hydroxy-2(or 5)-ethyl-5(or 2)-methyl-3(2H)furanone, 2-hydroxy-3-methyl-2-cyclopentenones, 3-hydroxy-4,5-dimethyl-2(5H)-furanone, fruit esters and fruit lactones (e.g. acetic acid-n-butylester, acetic acid isoamylester, propionic acid ethylester, ethyl butyrate, butyric acid-n-butylester, butyric acid isoamylester, 3-methylethyl butyrate, n-caproic acid ethylester, n-caproic acid allylester, n-caproic acid-n-butylester, n-octanoic acid ethylester, ethyl-3-methyl-3-phenylglycidate, ethyl-2-trans-4-cis-decadienoate), 4-(p-hydroxyphenyl)-2-butanone, 1,1-dimethoxy-2,2,5-trimethyl-4-hexane, 2,6-dimethyl-5-hepten-1-al and phenylacetaldehyde.

The use of sweet-tasting substances selected from the group comprising:
(a) sucrose, lactose, D-glucose, D-tagatose and D-fructose, wherein these carbohydrates may also be in the form of natural or synthetically produced mixtures (e.g. as a honey, invert sugar syrup, highly enriched fructose syrups made from corn starch [high fructose corn syrup])
(b) erythritol, threitol, arabitol, ribitol, xylitol, sorbitol, mannitol, dulcitol and lactitol,
(d) sweeteners from the group comprising sodium cyclamate, acesulfame K, neohesperidin dihydrochalcone, saccharin sodium salt, aspartame, superaspartame, neotame, alitame, sucralose, stevioside,
is preferred, wherein the quantity of added (i) hesperetin and (ii) the salts thereof in the preparation is sufficient to enhance in sensory terms the sweet taste impression of the sweet-tasting substance(s). The total quantity of hesperetin of formula (I) and/or the salts thereof is preferably in the range of 0.1 to 500 ppm, particularly preferably in the range of 1 to 250 ppm, particularly preferably in the range of 5 to 100 ppm, based on the total weight of the preparation.

A synergistic increase in the sweet taste impression can be achieved in particular with these combinations (as mentioned above).

Preferred sweet-tasting substances have been indicated above. In general sweet-tasting substances (including natural sources of these substances) can, however, be for example: sweet-tasting carbohydrates or sugars (e.g. sucrose (synonymous with saccharose), trehalose, lactose, maltose, melizitose, melibiose, raffinose, palatinose, lactulose, D-fructose, D-glucose, D-galactose, L-rhamnose, D-sorbose, D-mannose, D-tagatose, D-arabinose, L-arabinose, D-ribose, D-glyceraldehyde, maltodextrin) or vegetable preparations primarily containing these carbohydrates (e.g. from sugar beet (*Beta vulgaris* ssp., sugar fractions, sugar syrup, molasses), from sugar cane (*Saccharum officinarum* ssp., e.g. molasses, sugar syrups), from sugar maple (*Acer* ssp.), from agave (agave juice concentrate), synthetic/enzymatic hydrolysates of starch or sucrose (e.g. invert sugar syrup, highly enriched fructose syrups made of corn starch), fruit concentrates (e.g. made of apples or pears, apple syrup, pear syrup), sugar alcohols (e.g. glycerol, erythritol, threitol, arabitol, ribitol, xylitol, sorbitol, mannitol, dulcitol, lactitol), proteins (e.g. miraculin, monellin, thaumatin, curculin, brazzein), sweeteners (magap, sodium cyclamate, acesulfame K, neohesperidin dihydrochalcone, saccharin sodium salt, aspartame, superaspartame, neotame, alitame, sucralose, stevioside, rebaudioside, lugduname, carrelame, sucrononate, sucrooctate, monatin, phyllodulcin), certain sweet-tasting amino acids (glycine, D-leucine, D-threonine, D-asparagine, D-phenylalanine, D-tryptophan, L-proline), other sweet-tasting low-molecular substances (e.g. hernandulcin, isocoumarins such as phyllodulcin or hydrangenol, dihydrochalcone glycosides, such as neohesperidin dihydrochalcone, glycyrrhizin, glycyrrhetinic acid ammonium salt or other glycyrrhetinic acid derivatives), liquorice extracts (*Glycyrrhizza glabra* ssp.), *Lippia dulcis* extracts, *Momordica* ssp. extracts or individual substances (in particular *Momordica grosvenori* [Luo Han Guo] and the mogrosides obtained therefrom), *Hydrangea dulcis* or *Stevia* ssp. (e.g. *Stevia rebaudiana*) extracts or individual substances.

The above-mentioned preferred flavourings are flavourings which give a sweet olfactory impression, i.e. flavourings which do not taste sweet in the narrower sense but suggest a sweet taste in the wider sense (including odour perception in particular).

The invention is based on the surprising recognition that the hesperetin of formula (I) (or the salts and mixtures thereof, as indicated above) to be used according to the invention superproportionally (i.e. synergistically) increase the sweet taste impression of sweet-tasting substances (as indicated above), but in particular of sugars such as sucrose, lactose, glucose, D-tagatose and fructose and sugar alcohols, such as e.g. glycerol, erythritol, threitol, arabitol, ribitol, xylitol, sorbitol, mannitol, dulcitol, lactitol even in very low concentrations (less than 0.05% by weight preferably less than 0.025% by weight, particularly preferably less than 0.01% by weight, compare in this regard also the concentration ranges indicated below) and it is thus possible to reduce the sugar content in corresponding foods and semi-luxury foods without reducing the sweet taste impression at the same time. In low concentrations (compare in this regard the preferred concentrations used below) hesperetin of formula (I) and the salts thereof to be used according to the invention exhibit only a very weak inherent taste.

The sweet taste of a sweet-tasting substance or the sweet olfactory impression of a flavouring which gives a sweet olfactory impression is preferably enhanced in a preparation used for nourishment (foods), oral hygiene or consumption (semi-luxury foods).

A preferred preparation is a (preferably ready-to-consume or ready-to-use) preparation used for nourishment, oral hygiene or consumption (in particular in one of the embodiments indicated above as being particularly preferred) comprising a total quantity of less than 0.05% by weight (500 ppm), preferably less than 0.025% by weight (250 ppm), in particular less than 0.01% by weight (100 ppm) of (i) hesperetin of formula (I) and (ii) the salts thereof, based on the total weight of the preparation.

Accordingly preferred is the use of hesperetin of formula (I) (and/or the salts and mixtures thereof, as indicated above) for enhancing the sweet taste of a sweet-tasting substance or the sweet olfactory impression of a flavouring which gives a sweet olfactory impression, in ready-to-consume foods and semi-luxury foods, wherein the concentration (i) of the hesperetin and/or (ii) of the salts thereof is less than 0.05% by weight, preferably less than 0.025% by weight, particularly preferably less than 0.02% by weight, and most particularly preferably less than 0.01% by weight, based on the total weight of the ready-to-consume foods and semi-luxury foods.

Even in these low concentrations the hesperetin and/or the salts thereof or corresponding mixtures used significantly enhance(s) the sensory effect of sweet-tasting substances or flavourings which give a sweet olfactory impression.

Particularly preferred are preparations used for foods, oral hygiene or consumption (as described above, in particular in embodiments indicated as being preferred) comprising a total quantity in the range of 0.1 to 500 ppm, preferably in the range of 1 to 250 ppm, particularly preferably in the range of 5 to 100 ppm, of (i) hesperetin of formula (I) and (ii) the salts thereof, based on the total weight of the preparation.

Owing to the use of (i) hesperetin of formula (I) and (ii) the salts thereof according to the invention it is in particular possible to reduce the content of sweet-tasting substances, but in particular of sugars such as sucrose, lactose, fructose and/or glucose or mixtures thereof by 5 to 60% (based on the sweet-tasting substance(s)), compared with a preparation without (i) hesperetin or (ii) the salts thereof to be used according to the invention, without the sweet taste impression being reduced in the process.

Preferred preparations according to the invention, which may be sugarfree, sugar-reduced or contain sugar and are used in particular for nourishment, oral hygiene or consumption, are selected from the group comprising:

(A) confectionery, e.g. white, milk or dark chocolates, filled chocolates (for example with flavoured fondant mass, of the After-Eight type), chocolate bars, other bar-type products, chewy sweets, fruit gums, hard and soft toffees, chewing gum, sugar drops, lollipops), capsules (preferably seamless capsules for direct consumption, preferably with a coating based on gelatines and/or alginate), chewing gum (e.g. in the form of strips, lozenges, pellets, cushions, balls, hollow balls), (B) alcoholic or non-alcoholic drinks or instant drinks, in particular coffee, tea, wine, wine-containing drinks, beer, beer-containing drinks, liqueurs, schnapps, brandies, fruit-containing soft drinks, isotonic drinks, soft drinks, nectars, fruit and vegetable juices with the exception of unaltered citrus (in particular orange) juice products, fruit or vegetable preparations, instant cocoa drinks, instant tea drinks, instant coffee drinks, (C) cereal products and/or nut products, in particular breakfast cereals, cornflakes, oat flakes, bulk muesli, muesli bars, nuts and raisins, sweet popcorn, nut bars, nut and fruit bars, pre-cooked finished rice products, (D) milk products, in particular milk drinks, dairy ice cream, ice cream for diabetics yoghurt, blancmange-type pudding, kefir, cream cheese, soft cheese, hard cheese, dried milk powder, whey, butter, butter milk, partially or wholly hydrolysed milk protein-containing products, (E) fruit and/or vegetable preparations, in particular preserves, jams for diabetics, sorbets, fruit sauces, fruit fillings with the exception of natural citrus products, ketchup, sauces, dried vegetables, frozen vegetables, pre-cooked vegetables, vegetables pickled in vinegar, preserved vegetables, (F) products based on fat or oil or emulsions thereof, in particular mayonnaise, remoulade, dressings, spice preparations, (G) an oral hygiene product, in particular in the form of toothpaste, tooth cream, tooth gel, tooth powder, tooth cleaning liquid, tooth cleaning foam, mouthwash, mouthwash concentrate, tooth cream and mouthwash as a 2-in-1 product, boiled sweet, mouth spray, dental floss, chewing gum or dental care chewing gum.

The quantity of (i) hesperetin of formula (I) and (ii) the salts thereof is preferably sufficient in a preparation according to the invention to significantly enhance the sweet taste or olfactory impression by at least 10%, based on a comparative formulation which, with an otherwise identical composition, contains neither hesperetin of formula (I), nor the salts thereof.

Particularly relevant therefore are preparations according to the invention which comprise at least one sweet-tasting substance, preferably a sugar such as sucrose, lactose, glucose and/or fructose, wherein the quantity of the sweet-tasting substance is not sufficient to impart a satisfactory sweet taste to a comparative preparation, which does not contain hesperetin of formula (I) (and/or a corresponding salt or corresponding mixture), but has an otherwise identical composition, wherein the quantity of the hesperetin of formula (I) present, (and/or of a corresponding salt or a corresponding mixture, preferably in one of the above embodiments indicated above as being preferred) in the preparation is sufficient to enhance in sensory terms the sweet taste impression of the sweet-tasting substance, preferably to the extent that, overall, a satisfactory sweet taste is imparted. It has already been stated above that the total quantity of (i) hesperetin of formula (I) and (ii) the salts thereof (component (a)) in the preparation is preferably sufficient to impart the same or an enhanced sweetness impression compared to a preparation which, with an otherwise identical composition, contains neither (i) hesperetin of formula (I) nor (ii) the salts thereof, but at least 1.5 times the quantity (preferably at least 1.2 times the quantity, particularly preferably at least 1.4 times the quantity) of sugar.

Preferred preparations according to the invention are preparations used for nourishment, oral hygiene or consumption, that which was stated above applying with respect to their compositions.

The preparations used according to the invention for nourishment, oral hygiene or consumption are generally products which are intended to be introduced into the human oral cavity, remain there for a certain time and are either subsequently consumed there (e.g. ready-to-consume foods) or are removed from the oral cavity again (e.g. chewing gum or toothpaste). It is understood that the use of the hesperetin of formula (I) and/or the salts thereof or corresponding mixtures to be used according to the invention is provided for all manner of products of this kind. These products include all substances or produce which is intended to be taken up in the processed, partially processed or unprocessed state by humans into the oral cavity. This also includes substances that are added to foods during their production, processing or cultivation and are intended for introduction into the human oral cavity.

It is understood that the hesperetin of formula (I) and/or the salts thereof or the corresponding mixtures to be used according to the invention can be used in particular in foods. Within the scope of the present text "foods" are taken to mean in particular substances which are intended to be swallowed and then digested by humans in an unaltered, prepared or processed state. In this regard foods are also taken to mean encapsulations, coatings, or other types of enclosure which are intended to also be swallowed, or with which swallowing is envisaged. Certain products which are conventionally removed from the mouth again (e.g. chewing gum) are to be understood as a food within the scope of the present text as it cannot be ruled out that they are at least partially swallowed.

The hesperetin of formula (I) and/or the salts thereof or corresponding mixtures to be used according to the invention are used in particular in ready-to-consume foods. A ready-to-consume food is in this case taken to mean a food which has already been fully composed with respect to the substances crucial to the taste. The term "ready-to-consume foods" also includes corresponding drinks and solid or semi-solid ready-to-consume foods. Examples include frozen products which have to be thawed and heated to the consumption temperature before consumption. Products such as yoghurt or ice cream as well as chewing gum or hard boiled candies also constitute ready-to-consume foods.

The hesperetin of formula (I) and/or the salts thereof to be used according to the invention can also be used in semi-finished food products. The term "semi-finished food product" refers in this case to foods which are intended for consumption only in the more processed state, following addition of flavourings or flavours that (co-)determine the sensory impression.

A preparation used for oral hygiene (oral hygiene product, also called an oral hygiene preparation) according to the invention is taken to mean a preparation for cleaning and taking care of the oral cavity and pharyngeal cavity and for freshening the breath. This expressly includes care of teeth and gums. Forms of administration of common oral hygiene formulations are creams, gels, pastes, foams, emulsions, suspensions, aerosols, sprays as well as capsules, granules, pastilles, tablets, sweets or chewing gum, although this list should not be understood as being limiting to the purposes of this invention.

Further conventional active ingredients, raw materials, auxiliaries and additives for preparations according to the invention used for nourishment, oral hygiene or consumption can be provided in quantities of 5 to 99.999999% by weight, preferably 10 to 80% by weight, based on the total weight of the preparation. The preparations may also comprise water in a quantity up to 99.999999% by weight, preferably 5 to 80% by weight, based on the total weight of the preparation.

Further preferred preparations according to the invention are semi-finished products, perfume, flavouring or flavour compositions or spice mixtures.

The term "semi-finished products" in this case includes in particular semi-finished food products, i.e. foods which are intended to be consumed only in the more processed state after addition of flavourings or flavours that (co-)determine the sensory impression.

Semi-finished products according to the invention may also be in spray-dried form. Preparations according to the invention may also be in the form of capsules, tablets (uncoated and coated tablets, e.g. gastric juice-resistant coatings), sugar-coated pills, granules, pellets, solid mixtures, dispersions in liquid phases, emulsions, powders, solutions, pastes or other preparations that can be swallowed or chewed as a food supplement.

Preparations according to the invention which are in the form of semi-finished products can be used in particular for enhancing the sweet taste impression of finished product preparations used for nourishment, oral hygiene or consumption which are produced by using the semi-finished product preparation.

Spray-dried, solid preparations according to the invention are particularly well suited as semi-finished products to the production of preparations according to the invention which can be used in particular for foods, oral hygiene or consumption. In the spray-dried semi-finished products the solubility in particular of the hesperetin of formula (I) and/or the salts thereof to be used according to the invention is significantly improved by the carriers and/or auxiliaries, in particular by maltodextrin, starch, natural or synthetic polysaccharides and/or plant gums, such as modified starches or gum arabic. The spray-dried, solid semi-finished products according to the invention preferably contain 50 to 95% by weight carriers, in particular maltodextrin and/or starch, 5 to 40% by weight auxiliaries, preferably natural or synthetic polysaccharides and/or plant gums, such as modified starches or gum arabic, and 1 to 45% by weight of hesperetin of formula (I) and/or the salts thereof to be used according to the invention, based on the total quantity of spray-dried, solid preparation.

Preparations according to the invention which are selected from the group comprising semi-finished products, perfume, flavouring or flavour compositions or spice mixtures comprise a total quantity in the range of 0.0001% by weight to 95% by weight, preferably 0.001% by weight to 80% by weight, particularly preferably 0.001% by weight to 50% by weight, of (i) hesperetin of formula (I) or (ii) the salts thereof, based on the total weight of the preparation.

Semi-finished products according to the invention usually comprise further flavours and/or flavourings, in particular flavourings which give a sweet olfactory impression (cf. above), and suitable solvents (e.g. ethanol, glycerol, 1,2-propylene glycol, lactic acid, alkyl esters of lactic acid, ethyl esters of organic fruit acids, such as diethylmalonate, diethyltartrate, diethylmalate, triethylcitrate, diethylsuccinate, diethylfumarate, diethylmaleate) and further auxiliaries (e.g. colourings, pigments, antioxidants, preservatives, emulsifiers, viscosity-influencing substances).

Spray-dried, solid semi-finished products according to the invention preferably comprise 1 to 50% by weight of hesperetin and/or the salts thereof and corresponding mixtures to be used according to the invention, based on the total weight of the preparation, 0 to 10% by weight, preferably 1 to 10% by weight of other flavours, 50 to 99% by weight of carriers and 0 to 50% by weight, preferably 1 to 50% by weight, of further auxiliaries and/or stabilisers, in each case based on the total weight of the preparation.

Advantageous carriers in the spray-dried, solid preparations according to the invention are carbohydrates and/or carbohydrate polymers (polysaccharides). Examples of preferred carriers in the flavour particles to be used according to the invention are hydrocolloids, such as starches, broken down starches, chemically or physically modified starches, modified celluloses, gum arabic, ghatti gum, traganth, karaya, carrageenan, guar gum, locust bean gum, alginates, pectin, inulin or xanthan gum, dextrins and maltodextrins.

The degree of starch breakdown is measured using the characteristic number "dextrose equivalent" (DE) which can assume the limiting value 0 for the long chain glucose polymer starch and 100 for pure glucose.

Particularly preferred carriers for the spray-dried, solid preparations according to the invention are maltodextrins, wherein maltodextrins with DE values in the range of 10 to 30 are in turn advantageous here.

It has already been mentioned that spray-dried, solid semi-finished products are particularly suitable for producing preparations according to the invention which are to be used for nourishment, oral hygiene or consumption.

As already mentioned, the (i) hesperetin of formula (I) and/or the salts thereof are not always very soluble in conventional solvents (suitable for consumption). Therefore the connected object is posed within the framework of the present invention of improving the solubility of the (i) hesperetin of formula (I) and/or the salts thereof and corresponding mixtures to be used according to the invention, in particular in perfume, flavouring or flavour compositions, but also generally in preparations used in nourishment, oral hygiene or consumption. This object is achieved according to the invention by the use of an additional component (d) in a preparation according to the invention, wherein component (d) comprises specific esters and/or solvents.

A preferred preparation according to the invention comprises as additional component (d)
one or more ester(s) selected from the group comprising lactic acid-$C_1$-$C_6$-esters, tartaric acid-di-$C_1$-$C_4$-esters, succinic acid-di-$C_1$-$C_4$-esters, malonic acid-di-$C_1$-$C_4$-esters, malic acid-di-$C_1$-$C_4$-esters, citric acid-di-$C_1$-$C_4$-esters and citric acid-tri-$C_1$-$C_4$-esters,
and/or
one or more solvents selected from the group comprising 1,2-propylene glycol, dimethylsulphoxide, ethanol, lactic acid, and ethanol/water mixtures.

Apart from the additional component (d) there are preferably one or more further flavouring(s), in particular flavourings which give a sweet olfactory impression and are preferably selected from the above-given group of flavourings of this type.

Particularly preferred for increasing the solubility of the hesperetin of formula (I) and/or the salts thereof or corresponding mixtures to be used according to the invention are esters selected from the group comprising ethyl lactate, n-propyl lactate, n-butyl lactate, diethyltartrate, dimethylsuccinate, diethylsuccinate, dimethylmalonate, diethylmalonate, dimethylmalate, diethylmalate, and triethylcitrate and the solvent 1,2-propylene glycol.

Said esters can be in the form of all possible stereoisomers as pure substances or mixtures of the possible stereoisomers, depending on the underlying acid.

Perfume, flavouring or flavour compositions according to the invention which include the above-mentioned esters or solvents, induce very good solubility and prevent a significant tendency toward recrystallisation of the hesperetin of formula (I) and/or the salts thereof and corresponding mixtures to be used according to the invention. They are therefore particularly suitable for incorporation into preparations used according to the invention for nourishment, oral hygiene or consumption. Reference is made to the above statements with respect to the preferred concentrations of hesperetin or salts in perfume, flavouring or flavour compositions according to the invention.

Preparations according to the invention which are used for nourishment, oral hygiene or consumption are preferably produced by incorporating the hesperetin of formula (I) and/or the salts thereof or corresponding mixtures as a substance, a solution (e.g. in ethanol, water, lactic acid, 1,2-propylene glycol, dimethylsulphoxide, optionally in the presence of one of the above-mentioned esters or solvents) or in the form a mixture with a solid or liquid carrier (e.g. maltodextrin, starch, silica gel), flavours or flavourings and optionally further auxiliaries and/or stabilisers (e.g. natural or synthetic polysaccharides and/or plant gums, such as modified starches or gum arabic), i.e. in the form of a semi-finished product, in a base preparation used for nourishment, oral hygiene or consumption. Preparations according to the invention in the form of a solution and/or suspension or emulsion can advantageously firstly be converted by spray drying into a solid preparation according to the invention (semi-finished product), before this is in turn used for the production of preparations used according to the invention for nourishment, oral hygiene or consumption. Reference is made to the above statements with respect to the particular suitability of spray-dried semi-finished products for producing preparations used for nourishment, oral hygiene or consumption.

According to a further preferred embodiment the hesperetin of formula (I) and/or the salts thereof to be used according to the invention and optionally other components of the preparation according to the invention are firstly incorporated into emulsions, liposomes, e.g. starting from phosphatidylcholin, into microspheres, nanospheres or else into capsules, granules or extrudates of a matrix suitable for foods and semi-luxury foods, e.g. of starch, starch derivatives (e.g. modified starch), cellulose or cellulose derivates (e.g. hydroxypropyl cellulose), other polysaccharides (e.g. dextrin, alginate, curdlan, carrageenan, chitin, chitosan, pullulan), natural fats, natural waxes (e.g. beeswax, carnauba wax), of proteins, e.g. gelatines or other natural products (e.g. shellac) for producing the preparations according to the invention. In the process the products may be obtained, depending on the matrix, by spray drying, spray granulation, melt granulation, fluidised bed processes (e.g. according to WO 97/16078 or WO 2004/022642), fluidised bed spray granulation (e.g. according to WO 00/36931 or U.S. Pat. No. 4,946,654), coacervation, coagulation, extrusion, melt extrusion (e.g. according to WO 2003/092412, EP 1 123 660 or EP 1 034 705), emulsion processes, coating or other suitable encapsulation processes and optionally a suitable combination of said processes. In a further preferred production process for a preparation according to the invention the hesperitin or the salts thereof to be used according to the invention is/are firstly complexed with one or more suitable complexing agent(s), for example with cyclodextrins or cyclodextrin derivatives, preferably alpha- or beta-cyclodextrin, and used in this complexed form.

In some cases a preparation according to the invention is preferably one in which the matrix is selected such that the hesperetin of formula (I) and/or the salts thereof to be used according to the invention are released from the matrix with a delay, so a long-lasting effect is achieved. Particularly preferred is a fat, wax, polysaccharide or protein matrix in this regard.

Conventional raw materials, auxiliaries and additives for foods or semi-luxury foods can be used as further components for preparations according to the invention used for nourishment or consumption, e.g. water, mixtures of fresh or processed, vegetable or animal basic or raw materials (e.g. raw, roasted, dried, fermented, smoked and/or cooked meat, bones, cartilage, fish, vegetables, fruit, herbs, nuts, vegetable or fruit juices or pastes or mixtures thereof), digestible or indigestible carbohydrates (e.g. saccharose, maltose, fructose, glucose, dextrins, amylose, amylopectin, inulin, xylanes, cellulose, tagatose), sugar alcohols (e.g. sorbitol, erythritol), natural or hardened fats (e.g. tallow, lard, palm butter, coconut oil, hydrogenated vegetable fat), oils (e.g. sunflower oil, groundnut oil, corn oil, olive oil, fish oil, soya oil, sesame oil), fatty acids or salts thereof (e.g. potassium stearate), proteinogenic or non-proteinogenic amino acids and related compounds (e.g. γ-aminobutyric acid, taurine), peptides (e.g. gluthathion), natural or processed proteins (e.g. gelatines), enzymes (e.g. peptidases), nucleic acid, nucleotides, taste corrigents for unpleasant taste impressions, further taste modulators for further, generally not unpleasant taste impressions, other taste-modulating substances (e.g. inositolphosphate, nucleotides, such as guanosinmonophosphate, adenosinmonophosphate or other substances, such as sodium glutamate or 2-phenoxypropionic acid), emulsifiers (e.g. lecithins, diacylglycerols, gum arabic), stabilisers (e.g. carrageenan, alginate), preservatives (e.g. benzoic acid, sorbic acid), antioxidants (e.g. tocopherol, ascorbic acid), chelators (e.g. citric acid), organic or inorganic acid (e.g. malic acid, acetic acid, citric acid, tartaric acid, phosphoric acid), bitter principles (e.g. quinine, caffeine, limonine, amarogentine, humolone, lupolone, catechins, tannins), mineral salts (e.g. sodium chloride, potassium chloride, magnesium chloride, sodium phosphates), enzymatic browning-preventing substances (e.g. sulphite, ascorbic acid), etheric oils, plant extracts, natural or synthetic colourings or pigments (e.g. carotinoids, flavonoids, anthocyans, chlorophyll and the derivatives thereof), spices, trigeminally active substances or plant extracts containing such trigeminally active substances, synthetic, natural or nature-identical flavourings or perfumes and odour corrigents.

Dental care products (as an example of an oral hygiene product according to the invention) which contain the hesperetin of formula (I) and/or the salts thereof to be used according to the invention generally comprise an abrasive system (abrasive or polish), such as e.g. silicic acids, calcium carbonates, calcium phosphates, aluminium oxides and/or hydroxylapatites, surface-active substances, such as e.g. sodium laurylsulphate, sodium laurylsarcosinate and/or cocamidopropyl betaine, humectants, such as e.g. glycerol and/or sorbitol, thickeners, such as e.g. carboxymethyl cellulose, polyethylene glycols, carrageenan and/or Laponite®, sweeteners, such as e.g. saccharin, taste corrigents for unpleasant taste impressions, taste corrigents for further, generally not unpleasant taste impressions, taste-modulating substances (e.g. inositolphosphate, nucleotides such as guanosinmonophosphate, adenosinmonophosphate or other substances such as sodium glutamate or 2-phenoxypropionic acid), cooling active ingredients, such as e.g. menthol, menthol derivatives (e.g. L-menthol, L-menthyllactate, L-menthylalkyl carbonates, menthone ketals, menthanecarbonic acid amides), 2,2,2-trialkylacetic acid amides (e.g. 2,2-diisopropylpropionic acid methylamide), icilin and icilin derivatives, stabilisers and active ingredients, such as e.g. sodium fluoride, sodium monofluorophosphate, tin difluoride, quaternary ammonium fluorides, zinc citrate, zinc sulphate, tin pyrophosphate, tin dichloride, mixtures of various pyrophosphates, triclosan, cetylpyridinium chloride, aluminium lactate, potassium citrate, potassium nitrate, potassium chloride, strontium chloride, hydrogen peroxide, flavours and/or sodium bicarbonate or odour corrigents.

Chewing gums (as a further example of preparations used for oral hygiene), which contain the hesperetin of formula (I) and/or the salts thereof to be used according to the invention generally comprise a chewing gum base, i.e. a chewing compound that plasticises on chewing, various types of sugar, sugar substitutes, other sweet-tasting substances, sugar alcohols, taste corrigents for unpleasant taste impressions, other taste modulators for further, generally not unpleasant taste impressions, taste-modulating substances (e.g. inositolphosphate, nucleotides such as guanosinmonophosphate, adenosinmonophosphate or other substances such as sodium glutamate or 2-phenoxypropionic acid), humectants, thickeners, emulsifiers, flavours and stabilisers or odour corrigents.

A particularly preferred preparation according to the invention comprises at least one further substance for masking or reducing a bitter, metallic, chalky, acidic or astringent taste impression or for enhancing a sweet, salty or savoury taste impression. The hesperetin and/or the salts thereof or corresponding mixtures to be used according to the invention is/are thus used in combination with at least one (further) substance suitable for masking or reducing an unpleasant (bitter, chalky, acidic, astringent) taste impression or for enhancing a pleasant taste impression (sweet, salty, savoury). These specific preparations are eminently suitable for achieving a particularly effective enhancement of the sweetness in the preparations, according to the invention, containing sweet-tasting substances. The combination in particular of the hesperetin and/or the salts thereof to be used according to the invention with taste corrigents for unpleasant, in particular bitter, taste impressions, or flavour enhancers for pleasant, in particular sweet, taste impressions, is preferred.

Particularly preferred are preparations according to the invention which comprise 4-hydroxydihydrochalcones (see below for structure) or the salts thereof.

4-hydroxydihydrochalcones have the following structural formula:

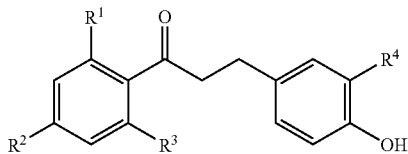

wherein $R^1$, $R^2$, $R^3$ and $R^4$ independently of each other represent H, OH or O-alkyl (with preferably 1 to 4 carbon atoms in each case, i.e. preferably $C_1$ to $C_4$ alkoxy), with the proviso that at least one of the radicals represents $R^1$, $R^2$ or $R^3$ OH.

A particularly preferred combination thus results owing to the use of the hesperetin of formula (I) and/or the salts thereof or corresponding mixtures, together with 4-hydroxydihydrochalcones or salts thereof (in particular the $Na^+$, $K^+$, $NH_4^+$, $Ca^{2+}$, $Mg^{2+}$, $Al^{3+}$ and/or $Zn^{2+}$ salts) for enhancing the sweetness of the above-mentioned sweet-tasting substances, in particular of sugars. Reference is also made to U.S. Provisional Application 60/784,444 and the documents based thereon (Symrise) with respect to the sweet-enhancing effect of 4-hydroxydihydrochalcones. The total content of hesperetin of formula (I) and/or the salts thereof or corresponding mixtures is in this case preferably at most 0.01% by weight (100 ppm) and the total content of 4-hydroxydihydrochalcones or the salts thereof preferably at most 0.01% by weight (100 ppm), in each case based on the total weight of the preparation. The indicated total contents relate in this case to ready-to-use preparations used for nourishment, oral hygiene or consumption. In semi-finished products, perfume, flavouring or flavour compositions the total content is correspondingly much higher. The ratio of the total quantity of the (i) hesperetin of formula (I) and (ii) the salts thereof to the total quantity of 4-hydroxydihydrochalcones or salts thereof used is preferably in the range of 1000:1 to 1:1000, preferably in the range of 10:1 to 1:10, particularly preferably in the range of 5:1 to 1:5, and more particularly preferably in the range of 7:3 to 3:7.

The (further) taste corrigents are selected for example from the following list: nucleotides (e.g. adenosin-5'-monophosphate, cytidin-5'-monophosphate) or the pharmaceutically acceptable salts thereof, lactisoles, sodium salts (e.g. sodium chloride, sodium lactate, sodium citrate, sodium acetate, sodium gluconoate), further hydroxyflavanones (e.g. eriodictyol, homoeriodictyol or the sodium salts thereof), in particular according to US 2002/0188019, hydroxybenzoic acid amides according to DE 10 2004 041 496 (e.g. 2,4-dihydroxybenzoic acid vanillylamide, 2,4-dihydroxybenzoic acid-N-(4-hydroxy-3-methoxybenzyl)amide, 2,4,6-trihydroxybenzoic acid-N-(4-hydroxy-3-methoxybenzyl)amide, 2-hydroxy-benzoic acid-N-4-(hydroxy-3-methoxybenzyl)amide, 4-hydroxybenzoic acid-N-(4-hydroxy-3-methoxybenzyl)amide, 2,4-dihydroxybenzoic acid-N-(4-hydroxy-3-methoxybenzyl)amide-mono-sodium salt, 2,4-dihydroxybenzoic acid-N-2-(4-hydroxy-3-methoxyphenyl) ethylamide, 2,4-dihydroxybenzoic acid-N-(4-hydroxy-3-ethoxybenzyl)amide, 2,4-dihydroxybenzoic acid-N-(3,4-dihydroxybenzyl)amide and 2-hydroxy-5-methoxy-N-[2-(4-hydroxy-3-methoxyphenyl)ethyl]amide (aduncamide), 4-hydroxybenzoic acid vanillylamide), bitter-masking hydroxydeoxybenzoins according to U.S. Provisional Application 60/668,189 and the documents based thereon (Symrise) (e.g. 2-(4-hydroxy-3-methoxyphenyl)-1-(2,4,6-trihydroxyphenyl)ethanone, 1-(2,4-dihydroxyphenyl)-2-(4-hydroxy-3-methoxyphenyl)ethanone, 1-(2-hydroxy-4-methoxyphenyl)-2-(4-hydroxy-3-methoxyphenyl) ethanone), amino acids (e.g. gamma-aminobutyric acid according to WO 2005/096841 for reducing or masking an unpleasant taste impression such as bitterness), malic acid glycosides according to WO 2006/003107, salty tasting mixtures according to U.S. Provisional Application 60/728,744 and the documents based thereon (Symrise), diacetyltrimers according to PCT/EP 2005/056355 and the documents based thereon (Symrise), mixtures of whey proteins with lecithins and/or bitter-masking substances, such as gingerdione according to U.S. Provisional Application 60/696,670 and the documents based thereon (Symrise).

It has already been stated several times that preparations according to the invention are selected in particular from the group comprising preparations used for nourishment, oral hygiene or consumption, semi-finished products, perfume, flavouring or flavour compositions or spice mixtures. Preparations according to the invention that are preferred are indicated hereinafter: bread, cakes and pastries (e.g. bread, biscuits, cake, muffins, waffles, baking mixtures, other bakery items), confectionery (e.g. white, milk or dark chocolates, filled chocolates (for example with flavoured fondant mass, of the After-Eight type), chocolate bars, other bar-type products, chewy sweets, fruit gums, hard and soft toffees, chewing gum, sugar drops, lollipops), capsules (preferably seamless capsules for direct consumption, preferably with a coating based on gelatines and/or alginate), fat compounds (e.g. fillings for bread, cakes and pastries for e.g. biscuit fillings, chocolate fat fillings, bar fat fillings), toppings, alcoholic or non-alcoholic drinks (e.g. coffee, tea, wine, wine-containing drinks, beer, beer-containing drinks, liqueurs, schnapps, brandies, fruit-containing soft drinks, isotonic drinks, soft drinks, nectars, fruit and vegetable juices (fruit or vegetable preparations with the exception of natural citrus products), instant drinks or instant powders (e.g. instant cocoa drinks, instant tea drinks, instant coffee drinks, instant desserts in powder form, such as blancmange powder or jelly), meat products (e.g. ham, fresh sausage or raw sausage preparations, pickled or marinated fresh or salt meat products), eggs or egg products (e.g. dried egg powder), cereal products and/or nut products (e.g. breakfast cereals, cornflakes, oat flakes, bulk muesli, muesli bars, nuts and raisins, sweet popcorn, nut bars, nut and fruit bars, pre-cooked finished rice products), milk products (e.g. milk drinks, dairy ice cream, yoghurt, blancmange, kefir, cream cheese, soft cheese, hard cheese, dried milk powder, whey, butter, buttermilk, partially or wholly hydrolysed milk protein-containing products), products made of soya protein or other soybean fractions (e.g. soya milk and products produced therefrom, soya lecithin-containing preparations, fermented products such as tofu or tempe or products produced therefrom, soya sauces), fruit preparations (e.g. preserves, sorbet, fruit sauces, fruit fillings with the exception of natural citrus products), vegetable preparations (e.g. ketchup, sauces, dried vegetables, pre-cooked vegetables, vegetables pickled in vinegar, preserved vegetables), snacks (e.g. baked or fried potato crisps or potato dough products, bread dough products, extrudates based on corn or groundnuts), products based on fat and oil or corresponding emulsions (e.g. mayonnaise, remoulade, dressings, spice preparations), other ready-to-eat meals and soups (e.g. dried soups, instant soups, pre-cooked soups), condiments, spice mixtures and in particular seasonings which are used for example in the snacks sector.

Preparations according to the invention may also be in the form of capsules, tablets (uncoated and coated tablets, e.g. gastric juice-resistant coatings), sugar-coated pills, granules, pellets, solid mixtures, dispersions in liquid phases, emulsions, powders, solutions, pastes or other preparations that can be swallowed or chewed as a food supplement.

The present invention also relates to a process for enhancing the sweet taste or sweet olfactory impression of a flavouring which gives a sweet olfactory impression, comprising the following step:

mixing one or more sweet-tasting substance(s) (component (b)) or one or more flavouring(s) which give(s) a sweet olfactory impression (component (c)) with a total quantity of a component (a) as it is defined above, i.e. with a total quantity of a hesperetin of formula (I) and/or (ii) a corresponding salt or corresponding mixture, wherein the total quantity of component (a) in the preparation is sufficient to enhance in sensory terms the sweet taste impression of the sweet-tasting substance(s) (b) or the sweet olfactory impression of the flavouring(s) (c) which give(s) a sweet olfactory impression.

See above with regard to the preferred quantities of hesperetin of formula (I) and/or the salts thereof and corresponding mixtures to be used according to the invention. A total concentration of at least 5 ppm and at most 100 ppm in a ready-to-use preparation used for oral hygiene or ready-to-consume preparation used for nourishment or consumption is often particularly preferred.

Overall however, the statements made above with respect to the use according to the invention and the preparations according to the invention also apply to the process according to the invention.

EXAMPLES

The examples serve to clarify the invention, without limiting it thereby. Unless stated otherwise, all details refer to the weight.

The hesperetin used in the following examples had a purity of >90, preferably >95% by weight and an amount of rotation of $[\alpha]_D^{25}$ between −20 and −60° (c=1% in ethanol, I=1 dm). An amount of rotation of −37.6° is given in the literature (Merck Index, 12th edition, Merck & Co., page 798, entry 4704).

Application Example 3

Spray-Dried Preparations as Semi-Finished Products for Flavouring Finished Goods

| Ingredient | Preparation (Content in % by weight) | | | |
|---|---|---|---|---|
| | A | B | C | D |
| Drinking water | 60.8% | 60.8% | 60.8% | 60.8% |
| Maltodextrin from wheat | 24.3% | 24.3% | 24.3% | 24.3% |
| Gum arabic | 6.1% | 6.1% | 6.1% | 6.1% |
| Hesperetin | 8.8% | 4.4% | 2.2% | 4.4% |
| Phloretin | — | 4.4% | 4.4% | — |

The drinking water was placed in a container and the maltodextrin and the gum arabic dissolved therein. Hesperetin and/or phloretin were then emulsified into the carrier solution using a Turrax. The temperature of the spray solution should not exceed 30° C. The mixture was subsequently spray-dried (desired temperature at inlet: 185-195° C., desired temperature at outlet: 70-75° C.). The spray-dried semi-finished product contained ca 18-22% hesperetin.

Application Example 4

Spray-Dried Preparation as a Semi-Finished Product for Flavouring Finished Goods by Using Further Taste-Modulating Substances

| Ingredient | Preparation (Content in % by weight) | | | | | |
|---|---|---|---|---|---|---|
| | A | B | C | D | E | F |
| Drinking water | 60.8 | 60.8 | 60.8 | 60.8 | 60.8 | 60.8 |
| Maltodextrin from wheat | 24.3 | 24.3 | 24.3 | 24.3 | 24.3 | 24.3 |
| Gum arabic | 6.1 | 6.1 | 6.1 | 6.1 | 6.1 | 6.1 |
| Hesperetin | 4.4 | 6.4 | 3.2 | 4.4 | 4.4 | 4.4 |
| Gamma-aminobutyric acid | 4.4 | | | | | |
| Homoeriodictyol | | 2.4 | 2.4 | | | |
| Divanillin | | | | 4.4 | | |
| 2,4-dihydroxybenzoic acid-N-(4-hydroxy-3-methoxybenzyl)amide | | | | | 2.2 | |
| 6-(4-hydroxy-3-methoxyphenyl)-hexan-2,4-dione | | | | | 2.2 | |
| Diacetyltrimer of formula | | | | | | 4.4 |

The drinking water was placed in a container and the maltodextrin and the gum arabic dissolved therein. The flavourings were subsequently emulsified into the carrier solution using a mixer (Turrax). The temperature of the resultant mixture should not exceed 30° C. The mixture was then spray-dried (desired temperature at inlet: 185-195° C., desired temperature at outlet: 70-75° C.). The spray-dried semi-finished product contained ca 18-22% flavourings.

Application Example 5

Combinations with Sweet-Tasting Substances as Sweeteners

| Ingredient | Preparation (Content in % by weight) | | | | |
|---|---|---|---|---|---|
| | A | B | C | D | E |
| Sucrose | 89.9 | 89.9 | 89.9 | | 50 |
| Fructose | 10 | 10 | 10 | | |
| Tagatose | | | | | |
| High fructose corn syrup | | | | 99.9 | |
| Maltitol | | | | | |
| Sorbitol | | | | | 49.95 |
| Hesperetin | 0.1 | 0.05 | 0.05 | 0.05 | 0.025 |
| Phloretin | | 0.05 | | 0.05 | 0.025 |

The ingredients were mixed in the given order. The resultant product can be used as a sweetener for foods or semi-luxury foods, e.g. coffee or tea.

As an example of use, tea and the product were mixed and packed in teabags made of filter paper. For use, 100-250 ml boiling water was poured onto a teabag and allowed to draw for 2-5 min.

Application Example 6

Flavour Mixtures for Enhancing Sweetness

| Ingredient | Preparation (% by weight) | | | | | | | | | |
|---|---|---|---|---|---|---|---|---|---|---|
| | A | B | C | D | E | F | G | H | I | J |
| Vanilla flavour (e.g. obtainable from Symrise) | 75.00 | 75.00 | | | | | | | | |
| Sugar flavour of the black treacle type | | | | | | | | | | |
| Ethyl lactate | | | 1.00 | 0.50 | 0.050 | | 0.50 | 1.00 | 0.05 | 0.05 |
| n-Propyl lactate | | | 0.50 | | | | 0.50 | 0.50 | | |
| n-Butyl lactate | | | 0.30 | 0.30 | 0.030 | 1.80 | 0.30 | 0.30 | 0.03 | 0.03 |
| Diethylmalate | | | 1.00 | | | 1.00 | 0.50 | 1.00 | | |
| Diethyltartrate | | | 0.50 | | | | 0.50 | 0.50 | | |
| Diethylsuccinate | | | 0.50 | | | | | 0.50 | 10.0 | |
| Diethylmalonate | | | 0.50 | | | 2.00 | | 0.50 | | |
| Triethylcitrate | | | 0.50 | | | | 0.50 | 0.50 | | |
| Lactic acid | | | 1.00 | 2.00 | 0.20 | 2.00 | | 2.00 | 0.20 | 10.0 |
| Phloretin | | 0.30 | | 1.25 | | 1.25 | | 0.50 | 2.50 | |
| Hesperetin | 0.625 | 0.325 | 2.50 | 1.25 | 2.50 | 1.25 | 2.50 | 1.00 | 2.50 | 5.00 |
| 1,2-propylene glycol | ad 100 | ad 100 | ad 100 | ad 100 | ad 100 | ad 100 | ad 100 | ad 100 | ad 100 | ad 100 |

The components indicated in the Table were mixed in the given order by way of stirring and optionally completely homogenised by heating to 20-50° C. Clear, generally colourless or yellow solutions were obtained which could be used as a flavour.

Application Example 7

Chewing Gums

Application Example 7a

| Part | Ingredient | % by weight |
|---|---|---|
| A | Chewing gum base, Company "Jagum T" | 30.00 |
| B | Sorbitol, pulverised | 39.00 |
| | Isomalt ® (Palatinit GmbH) | 9.50 |
| | Xylitol | 2.00 |
| | Mannitol | 3.00 |
| | Aspartame ® | 0.10 |
| | Acesulfame ® K | 0.10 |
| | Emulgum ® (Colloides Naturels, Inc.) | 0.30 |
| C | Sorbitol, 70% aqueous solution | 14.00 |
| | Glycerol | 1.00 |
| D | Curled mint flavour, containing 1% by weight hesperetin, based on the total weight of the flavour | 1.00 |

Parts A to D were mixed and intensively kneaded. The raw mixture may be processed, e.g. in the form of thin strips, into ready-to-consume chewing gums.

Application Example 7b

Non-Stick Chewing Gum

The chewing gum base K1 consisted of 2.0% butyl rubber (isobutene-isoprene-copolymer, MW 400000), 6.0% polyisobutene (MW=43800), 43.5% polyvinyl acetate (MW=12000), 31.5% polyvinyl acetate (MW=47000), 6.75% triacetin and 10.25% calcium carbonate. The chewing gum base K1 and the chewing gums may be produced analogously to U.S. Pat. No. 5,601,858.

| | I (% by weight) | II (% by weight) | III (% by weight) |
|---|---|---|---|
| Chewing gum base K1 | 26.00 | 26.00 | 26.00 |
| Triacetin | 0.25 | 0.25 | 0.25 |
| Lecithin | 0.50 | 0.50 | 0.50 |
| Sorbitol, crystalline | 40.90 | 40.60 | 40.50 |
| Mannitol | 15.30 | 15.20 | 15.10 |
| Glycerol | 12.10 | 12.00 | 11.80 |
| Aspartame | 0.17 | 0.17 | 0.17 |
| Encapsulated aspartame | 1.08 | 1.08 | 1.08 |
| Amorphous silica | 1.00 | 1.00 | 1.00 |
| Cotton seed oil | 0.50 | 0.50 | 0.50 |
| Polyoxyethylene-sorbitan-monolaurate (E-432) | 1.00 | 1.00 | 1.00 |
| Encapsulated spearmint flavour (contains L-carvone) | 0.20 | 0.10 | 0.30 |
| Encapsulated winter green flavour (contains methylsalicylate) | — | 0.40 | — |
| Peppermint oil containing 1% by weight hesperetin, based on the total weight of the flavour | 1.00 | 1.20 | 1.50 |
| L-menthyl-L-lactate | 0.10 | — | 0.30 |

Application Example 7c

Bubble Gum

The bubble gum can be produced analogously to U.S. Pat. No. 5,093,136.

|  | I (% by weight) | II (% by weight) |
| --- | --- | --- |
| Styrene-Butadiene-Copolymer (SBR) | 19.50 | 17.50 |
| Polyisobutene | 8.00 | 8.00 |
| Sorbitol powder | 49.19 | 47.19 |
| Sorbitol, 70%, in water | 9.20 | 22.20 |
| Hydrogenated starch hydrolysates (HSH) | 9.00 | — |
| Glycerol | 3.00 | 2.00 |
| Aspartame | 0.10 | 0.10 |
| Encapsulated aspartame | 0.50 | 0.50 |
| Red and blue colouring | 0.01 | 0.01 |
| Strawberry-raspberry flavour containing 1% by weight hesperetin, based on the total weight of the flavour | 1.50 | 2.50 |

The chewing gums of recipe (I) were removed from the mould as compact balls, those of recipe (II) as hollow balls.

Application Example 7d

Chewing Gum

The chewing gum base K2 consisted of 28.5% terpene resin, 33.9% polyvinyl acetate (MW=14000), 16.25% hydrogenated vegetable oil, 5.5% mono- and diglycerides, 0.5% polyisobutene (MW 75000), 2.0% butyl rubber (isobutene-isoprene copolymer), 4.6% amorphous silicon dioxide (water content ca 2.5%), 0.05% antioxidant tert.-tert.-butylhydroxytoluene (BHT), 0.2% lecithin, and 8.5% calcium carbonate. The chewing gum base K2 and the chewing gums can be produced analogously to U.S. Pat. No. 6,986,907.

|  | I (% by weight) | II (% by weight) | III (% by weight) |
| --- | --- | --- | --- |
| Chewing gum K2 | 25.30 | 27.30 | 26.30 |
| Sorbitol | 61.48 | 59.48 | 61.60 |
| Glycerol | 2.40 | 2.40 | 2.40 |
| Lecithin | 7.00 | 7.00 | 7.00 |
| Aspartame | 0.14 | 0.14 | 0.14 |
| Encapsulated aspartame | 0.68 | 0.68 | 0.48 |
| Menthol, spray-dried | 1.00 | 0.50 | 0.40 |
| Cherry flavour, spray-dried | — | 1.20 | — |
| Lemon flavour containing 1% by weight hesperetin, based on the total weight of the flavour | 1.20 | 1.30 | 1.68 |
| Orange oil, natural | 0.80 | — | — |

The chewing gums of recipes (I) and (II) were removed from the mould as strips, those of recipe (III) as pellets.

Application Example 8

Toothpaste

| Part | Ingredient | Content in % by weight |
| --- | --- | --- |
| A | Demineralised water | 22.00 |
|  | Sorbitol, 70% aqueous solution | 45.00 |
|  | Solbrol ® M, sodium salt (Bayer AG, p-hydroxybenzoic acid alkylester) | 0.15 |
|  | Trisodium phosphate | 0.10 |
|  | Saccharin, 450 fold | 0.20 |
|  | Sodium monofluorophosphate | 1.12 |
|  | Polyethylene glycol 1500 | 5.00 |
| B | Sident 9 (abrasive silicon dioxide) | 10.00 |
|  | Sident 22 S (thickening silicon dioxide) | 8.00 |
|  | Sodium carboxymethylcellulose | 0.90 |
|  | Titanium dioxide | 0.50 |
| C | Demineralised water | 4.53 |
|  | Sodium lauryl sulphate | 1.50 |
| D | Peppermint flavour containing 1% by weight hesperetin, based on the total weight of the flavour | 1.00 |

The ingredients of parts A and B were each pre-mixed on their own and thoroughly stirred together under vacuum at 25-30° C. for 30 min. Part C was pre-mixed and added to A and B; D was added and the mixture thoroughly stirred under vacuum at 25-30° C. for 30 min. Following relaxation the toothpaste was finished and could be decanted into containers.

Application Example 9

Sugar-Reduced Soft Drinks

Comparative preparation with normal sucrose content (A)
Comparative preparation with reduced sucrose content (B)
Preparations according to the invention (C-H)

|  | Preparation (Content in % by weight) | | | | | | | |
| --- | --- | --- | --- | --- | --- | --- | --- | --- |
| Ingredient | A | B | C | D | E | F | G | H |
| Water | 89.85 | 91.85 | 91.797 | 91.797 | 91.299 | 91.599 | 91.499 | |
| Sucrose | 10.0 | 8.0 | 8.0 | 8.0 | 8.0 | 8.0 | 8.0 | 8.0 |
| Citric acid | 0.15 | 0.2 | 0.2 | 0.2 | 0.2 | 0.2 | 0.2 | 0.2 |
| Fructose | | | | | | 0.2 | | |
| Tagatose | | | | | | | 0.3 | |
| Maltitol syrup | | | | | 0.5 | | | |
| Erythritol | | | | | | | | 0.5 |
| Hesperetin | — | — | 0.003 | 0.0015 | 0.0005 | 0.0005 | 0.001 | 0.0005 |
| Phloretin | — | — | — | 0.0015 | 0.0005 | 0.0005 | | 0.0005 |

The substances were placed in a container and topped up with water and dissolved.

Application Example 10

Use in a Sugar-Reduced Soft Drink Together with Other Flavourings and Flavours

| Ingredient | Content | Preparation | | | | | | | |
|---|---|---|---|---|---|---|---|---|---|
| | | A | B | C | D | E | F | G | H |
| Saccharose | % | 8 | 8 | 8 | 8 | 8 | 8 | 8 | 8 |
| Citric acid | % | 0.2 | 0.2 | 0.2 | 0.2 | 0.2 | 0.2 | 0.2 | 0.2 |
| Hesperetin 1% in 1,2-propylene glycol | % | 0.05 | 0.1 | 0.05 | 0.05 | 0.05 | 0.05 | 0.05 | 0.05 |
| Phloretin (compound 4) 1% in 1,2-propylene glycol | % | 0.05 | | 0.05 | 0.05 | 0.1 | 0.1 | 0.1 | 0.15 |
| Ethylhydroxymethyl-furanone | ppb | 0.01 | | | | | | | |
| Vanillin | ppb | 15 | | | | | | | |
| Diethylmalonate | ppb | | 70 | | | | | | |
| Phenylethylacetate | ppb | | 1 | | | | | | |
| 2-Methylbutanal | ppb | | | 0.3 | | 0.3 | | | |
| Isovaleraldehyde | ppb | | | 0.2 | | 0.2 | | | |
| Furfurylacetate | ppb | | | 0.3 | | | | | |
| Massoilactone | ppb | | | | 5 | 5 | | 5 | 5 |
| γ-Octalactone | ppb | | | | 5 | 5 | | 5 | 5 |
| Ethylbutyrate | ppb | | | 0.5 | | 05 | | 0.5 | |
| Maltol | ppb | 350 | | | | 350 | | 350 | |
| 2,5-dimethyl-4-hydroxy-2H-furan-3-one | ppb | 3 | | | | 3 | | 3 | |
| Ethylisobutyrate | ppb | | 0.1 | | | 0.1 | | 0.1 | |
| Ethyl-2-methylbutyrate | ppb | | 0.1 | | | 0.1 | | 0.1 | |
| 1,2-propylene glycol | % | 0.1 | 0.1 | 0.1 | 0.1 | 0.1 | 0.1 | 0.1 | 0.1 |
| Butylphenylacetate | ppb | | | | 10 | | | | |
| Acetanisol | ppb | | | | 20 | | | | |
| Methyl sorbate | ppb | | | | 100 | | | | |
| L-lysine | ppm | | | | | | 100 | 30 | |
| Malic acid | ppm | | | | | | 80 | | |
| L-arginine | ppm | | | | | | 5 | 20 | |
| L-asparagic acid | ppm | | | | | | 0.5 | | |
| Calcium chloride | ppm | | | | | | 20 | | |
| Glutamine | ppm | | | | | | 2 | | |
| Potassium hydrogen phosphate | ppm | | | | | | 6 | | |
| Magnesium chloride | ppm | | | | | | 20 | | |
| L-valine | ppm | | | | | | 0.5 | | |
| Glycine | ppm | | | | | | | 40 | |
| L-alanine | ppm | | | | | | | 20 | |
| L-serine | ppm | | | | | | | 50 | |
| Water | | Top up to 100% | | | | | | | |

The substances were placed in a container and topped up with water to 100% and dissolved. The product was decanted into bottles and carbonised as required.

Application Example 11

Sugar-Free Hard Boiled Candies

| Ingredient | Content (wt. %) |
|---|---|
| Palatinite, Type M | 75.10% |
| Water | 24.82% |
| Peppermint flavour | 0.1% |
| Hesperetin | 0.01% |

Palatinite was mixed with water and the mixture melted at 165° C. and subsequently cooled to 115° C. The peppermint flavour and hesperetin were added and after thorough mixing poured into moulds, removed from the moulds following hardening and subsequently individually packed.

Application Example 12

Sugar-Reduced Hot Blancmange-Type Pudding

Comparative preparation with normal sucrose content (A)
Comparative preparation with reduced sucrose content (B)
Preparation according to the invention with reduced sucrose content and hesperetin (C)
Preparation according to the invention with reduced sucrose content, D-tagatose and hesperetin (D)

| | Preparation (Content in % by weight) | | | |
|---|---|---|---|---|
| Ingredient | A | B | C | D |
| Sucrose | 7.8% | 5.4% | 5.4% | 5.4% |
| Starch | 3.0% | 3.0% | 3.0% | 3.0% |
| Skimmed milk powder | 1.5% | 1.5% | 1.5% | 1.5% |

-continued

| Ingredient | A | B | C | D |
|---|---|---|---|---|
| Aubygel MR50 | 0.5% | 0.5% | 0.5% | 0.5% |
| Vanilla pod extract, spray-dried, Symrise | 0.1% | 0.1% | 0.1% | 0.1% |
| Hesperetin | — | — | 0.02% | 0.01% |
| D-tagatose | — | — | — | 0.1% |
| Milk 1.5% fat content | Top up to 100% | Top up to 100% | Top up to 100% | Top up to 100% |

The solid substances were placed in a container and stirred together with the milk. The mixture was heated to 95° C. for 2 min while stirring thoroughly, decanted and cooled to 5-8° C.

The sweetness of the 7.8% sucrose-containing comparative preparation A could be achieved with a slightly delayed sweetness impression with preparation C during tasting by tasters. Preparation C was significantly sweeter compared with comparative preparation B. Preparation D was comparable to C, but had an improved initial sweetness.

Application Example 13

Low-Fat Yoghurts

Comparative preparation with sugar (A)
Preparations according to the invention with sweetener mixture and hesperetin (B-C)

| Ingredient | A | B | D |
|---|---|---|---|
| Sucrose | 10% | 8% | 6% |
| Tagatose | — | — | 0.5% |
| Fructose | — | — | 0.5% |
| Hesperetin | — | 0.01% | 0.005% |
| Phloretin | — | — | 0.005% |
| Yoghurt, 0.1% fat | Top up to 100% | Top up to 100% | Top up to 100% |

The ingredients were mixed and cooled at 5° C.

Application Example 14

Use Together with Sweeteners in Low-Fat Yoghurts

Comparative preparation with sweetener mixture (A)
Preparations according to the invention with sweetener mixture and hesperetin (B-C)

| Ingredient | A | B | D |
|---|---|---|---|
| D-tagatose | 0.482% | 0.482% | 0.482% |
| Sucralose | 0.003% | 0.003% | 0.003% |
| Aspartame | 0.005% | 0.005% | 0.005% |
| Acesulfame K | 0.01% | 0.01% | 0.01% |
| Hesperetin | — | 0.01% | 0.005% |
| Phloretin | — | — | 0.005% |
| Yoghurt, 0.1% fat | Top up to 100% | Top up to 100% | Top up to 100% |

The ingredients were mixed and cooled at 5° C.

Application Example 15

Milk Mix Drinks

Comparative preparations with sugar (A-B)
Preparations according to the invention with sugar and hesperetin (C-D)

| Ingredient | A | B | C | D |
|---|---|---|---|---|
| Sucrose | 10.0 | 8.0 | 8.0 | 7.0 |
| Fructose | — | — | — | 0.5 |
| Tagatose | — | — | — | 0.5 |
| Hesperetin | — | — | 0.01% | 0.005% |
| Phloretin | — | — | — | 0.005% |
| Long-life milk, 1.5% fat | Top up to 100% | | | |

The ingredients were mixed, topped up with milk, thoroughly stirred, decanted into bottles and stored cooled at 5° C.

Application Example 16

Sugar-Reduced Tomato Ketchup

Comparative preparation with sugar (A)
Comparative preparation with reduced sugar content (B)
Preparations according to the invention with sugar and hesperetin (C-I)

| Ingredient | A | B | C | E | F | G | H | I |
|---|---|---|---|---|---|---|---|---|
| Cooking salt | 2 | 2 | 2 | 2 | 2 | 2 | 2 | 2 |
| Starch, Farinex WM 55 | 1 | 1 | 1 | 1 | 1 | 1 | 1 | 1 |
| Sucrose | 12 | 9.6 | 9.2 | 8.4 | 9.6 | 9.6 | 8.4 | 8.4 |
| Tomato concentrate 2-fold | 40 | 40 | 40 | 40 | 30 | 30 | 30 | 30 |
| Glucose syrup 80 Brix | 18 | 18 | 18 | 18 | 18 | 18 | 18 | 18 |
| Wine vinegar 10% | 7 | 7 | 7 | 7 | 3 | 3 | 3 | 3 |
| Water | 20 | 22.4 | 22.4 | 23.2 | 36.0 | 36.0 | 37.2 | 37.2 |
| Hesperetin 2.5% in 1,2-propylene glycol | | 0.4 | 0.2 | 0.2 | 0.4 | 0.2 | 0.2 | 0.2 |
| Phloretin 2.5% in 1,2-propylene glycol | | | 0.2 | 0.2 | | | | 0.2 |

The ingredients were mixed in the given order and the finished ketchup homogenised using an agitator, decanted into bottles and sterilised.

Application Example 17

Sugar-Reduced Ice Cream

Comparative preparation with sugar (A)
Comparative preparation with reduced sugar content (B)
Preparations according to the invention with sugar and hesperetin (C-F)

| Ingredient | Preparation (Content in % by weight) | | | | | |
|---|---|---|---|---|---|---|
| | A | B | C | D | E | F |
| Skimmed milk | 57.15 | 61.15 | 60.95 | 60.95 | 60.95 | 60.95 |
| Vegetable fat, melting range 35-40° C. | 20.00 | 20.00 | 20.00 | 20.00 | 20.00 | 20.00 |
| Sugar (Saccharose) | 12.00 | 8.00 | 8.00 | 8.00 | 8.00 | 8.00 |
| Skimmed milk powder | 5.00 | 5.00 | 5.00 | 5.00 | 5.00 | 5.00 |
| Glucose syrup 72% dry substance | 5.00 | 5.00 | 5.00 | 5.00 | 5.00 | 5.00 |
| Emulsifier SE 30 (Grindstedt Products, Denmark) | 0.65 | 0.65 | 0.65 | 0.65 | 0.65 | 0.65 |
| Flavour containing 0.1% diacetyl and 1% vanillin | 0.20 | 0.20 | 0.20 | 0.20 | | |
| Flavour containing 0.1% diacetyltrimer (formula see Application Example 4), 0.1% diacetyl and 1% vanillin | | | | | 0.20 | 0.20 |
| Flavour according to Application Example 6, preparation E | | | 0.20 | | 0.20 | |
| Flavour according to Application Example 6, preparation H | | | | 0.20 | | 0.20 |

Skimmed milk and glucose syrup were heated to 55° C. and sugar, skimmed milk powder and emulsifier added. The vegetable fat was pre-heated and the entire mass heated to 58° C. After adding the flavour the mixture was homogenised using a through-flow high-pressure homogeniser (180/50 bar). The mass obtained was heated for 1 min at 78° C., subsequently cooled to 2-4° C. and incubated for 10 h at this temperature to age. The aged mass was then decanted and stored frozen at −18° C.

Application Example 18

Ice Cream Suitable for Diabetics

An ice cream suitable for diabetics was produced from the following ingredients and decanted into tubs in portions of 95 mL each:

Concentrated skimmed milk, fructose syrup, strawberry pieces and strawberry puree (15%), vegetable fat, diabetic chocolate chips (3.5%, with emulsifier with soya lecithin), whey product, red beet juice, locust bean gum, guar gum, carrageen, emulsifier (E 471), gelatines, acid, citric acid, strawberry flavour (containing 1% by weight hesperetin based on the total weight of the strawberry flavour), carotene colouring.

Nutritional value (per 95 mL):
Protein 1.8 g, carbohydrates 13.3 g (of which fructose 9.5 g), fat 4.2 g.

Application Example 19

Diabetic Chocolate Based on Maltitol

A chocolate suitable for diabetics was produced from the following ingredients and poured into rectangular blocks:

Maltitol, hazel nut compound, cocoa butter, skimmed milk powder, cocoa mass, inulin, concentrated butter, emulsifier soya lecithins, vanilla flavour (containing vanilla pod extract, vanillin and 1% by weight hesperetin, based on the total weight of the vanilla aroma).

Nutritional value (per 100 g):
Protein 8 g, carbohydrates 43 g (of which maltitol 34 g), fat 34 g.

Application Example 20

Diabetic Chocolate Based on Fructose

A chocolate suitable for diabetics was produced from the following ingredients and poured into rectangular blocks:

Cocoa mass, fructose, skimmed milk powder, cocoa butter, inulin, concentrated butter, emulsifier soya lecithin, walnuts, cooking salt, vanilla flavour (containing vanillin and 1% by weight hesperetin, based on the total weight of the vanilla flavour).

Nutritional value (per 100 g):
Protein 8.8 g, carbohydrates 34 g (of which fructose 23 g, lactose 7.5 g, saccharose 1.4 g), fat 36 g; fibre 18.5 (of which 12.2 g inulin); sodium: 0.10 g. Cocoa content at least 50% by weight.

Application Example 21

Sugar-Reduced Muesli Mixture

| No. | | A (% by weight) | B (% by weight) |
|---|---|---|---|
| 1 | Oat flakes | 17.00 | 18.90 |
| 2 | Crunchy oat flake clusters | 10.00 | 12.00 |
| 3 | Rice crispies | 16.90 | 17.80 |
| 4 | Cornflakes | 16.50 | 17.50 |
| 5 | Currants | 3.50 | 3.50 |
| 6 | Hazelnuts, chopped | 2.50 | 2.50 |
| 7 | Glucose syrup from wheat, DE 30 | 9.50 | 9.50 |
| 8 | Saccharose | 20.00 | 14.00 |
| 9 | Water | 4.00 | 4.00 |
| 10 | Citric acid powder, anhydrous | 0.10 | 0.10 |
| 11 | Flavour from Example 6, variant E | — | 0.20 |

Mix each of constituents No. 1 to 6 in a rotary drum (mixture 1). Heat each of constituents No. 7 to 9 and add constituent No. 10 (and in recipe B also add constituent No. 11) (mixture 2). Add mixture 2 to mixture 1 in each case and mix thoroughly. Finally place the resultant muesli mixture on a baking sheet and dry in an oven at 130° C. for 8 minutes.

The sweetness perception between the full sugar variation of recipe A and the muesli mixture with 30% less sugar of recipe B was graded by a group of experts as equally pronounced. No difference in the sweet impression was found in an additional triangular test.

Application Example 22

Sugar-Reduced Fruit Gums

The sweetness perception between the full sugar fruit gums of recipe A given hereinafter and the sugar-reduced fruit gums of recipe B (the saccharose content had been reduced by 76%) was graded in both cases by a group of experts as equally pronounced. No difference in the sweet impression was found in an additional triangular test.

| | A (% by weight) | B (% by weight) |
|---|---|---|
| Water | 23.70 | 25.70 |
| Saccharose | 34.50 | 8.20 |
| Glucose syrup, DE 40 | 31.89 | 30.09 |
| Iso Syrup C* Tru Sweet 01750 (Cerestar GmbH) | 1.50 | 2.10 |

-continued

|  | A (% by weight) | B (% by weight) |
|---|---|---|
| Gelatine 240 Bloom | 8.20 | 9.40 |
| Polydextrose (Litesse ® Ultra, Danisco Cultor GmbH) | — | 24.40 |
| Yellow and red colouring | 0.01 | 0.01 |
| Citric acid | 0.20 | |
| Flavour according to Application Example 6, preparation J | — | 0.10 |

Polydextrose is a polysaccharide which does not itself taste sweet and has a low calorific value.

Application Example 23

Chocolate-Cappuccino Ice Cream

The sweetness perception between the full-sugar ice cream of recipe A given hereinafter and the sugar-reduced ice cream of recipe B (saccharose content had been reduced by 25%) was graded in both cases by a group of experts as equally pronounced. No difference in the sweet impression was found in an additional triangular test.

|  | A (% by weight) | B (% by weight) |
|---|---|---|
| Glucose-fructose syrup | 14.10 | 14.10 |
| Saccharose | 10.00 | 7.50 |
| Skimmed milk powder | 5.00 | 5.00 |
| Cream (36% fat content) | 24.00 | 24.00 |
| Emulsifier and stabiliser Cremodan ® 709VEG (Danisco) | 0.50 | 0.50 |
| Cocoa powder | 5.975 | 5.975 |
| Carrageenan | 0.025 | 0.025 |
| Water | 40.20 | 42.50 |
| Cappuccino flavour | 0.20 | 0.20 |
| Hesperetin 2.5% in 1,2-propylene glycol/ethanol | — | 0.20 |

Application Example 24

Gelatine Capsules for Direct Consumption

|  | I (% by weight) | II (% by weight) | III (% by weight) |
|---|---|---|---|
| Gelatine casing: | | | |
| Glycerol | 2.014 | 2.014 | 2,.014 |
| Gelatine 240 Bloom | 7.91 | 7.91 | 7.91 |
| Sucralose | 0.065 | 0.065 | 0.065 |
| Allura red | 0.006 | 0.006 | 0.006 |
| Brilliant blue | 0.005 | 0.005 | 0.005 |
| Core composition: | | | |
| Vegetable oil triglyceride (coconut oil fraction) | 79.49 | 68.55 | 58.55 |
| Orange flavour, containing 1% by weight hesperetin, based on the total weight of the flavour | 10.0 | 20.0 | 28.65 |
| Neotame and aspartame | 0.01 | 0.05 | — |
| Sucralose | 0.10 | 0.15 | 0.40 |
| 2-hydroxypropyl-menthylcarbonate | 0.33 | 0.20 | — |
| 2-hydroxyethylmenthyl-carbonate | — | 0.20 | 1.00 |
| (1R,3R,4S) menthyl-3-carbonic acid-N-ethylamide (WS-3) | — | 0.55 | 0.50 |
| (−)-Menthone glycerol acetal (Frescolat MGA) | — | 0.30 | 0.80 |
| Vanillin | 0.07 | — | 0.10 |

The gelatine capsules suitable for direct consumption were produced according to WO 2004/050069 and had a diameter of 5 mm, the weight ratio of core material to casing material was 90:10. The capsules opened in the mouth within less than 10 seconds and dissolved completely within less than 50 seconds.

The invention claimed is:

1. A preparation comprising:
  (a) 0.1 to 500 ppm of hesperetin, or a salt thereof;
  (b) one or more sweet-tasting substances selected from the group consisting of sucrose, lactose, glucose, D-tagatose, fructose, and sugar alcohols;
    wherein the (a) hesperetin, or salt thereof, and the (b) one or more sweet-tasting substances in the preparation are in amounts such that the sweet taste impression of the preparation is enhanced by at least 20%, in comparison to a preparation with an otherwise identical composition without the (a) hesperetin, or salt thereof.

2. The preparation according to claim 1, wherein the (b) one or more sweet-tasting substances is selected from the group consisting of sucrose, lactose, glucose, D-tagatose, and fructose.

3. The preparation according to claim 2, wherein the (b) one or more sweet-tasting substances is sucrose.

4. The preparation according to claim 1, further comprising:
  (c) one or more flavorings that give a sweet olfactory impression.

5. The preparation according to claim 2, wherein the (c) one or more flavoring that give a sweet olfactory impression are selected from the group consisting of vanillin, ethylvanillin, ethylvanillin isobutyrate (3-ethoxy-4-isobutyryloxy-benzaldehyde), 2,5-dimethyl-4-hydroxy-3(2H)-furanone and derivatives, homofuronol (2-ethyl-5-methyl-4-hydroxy-3(2H)-furanone and 5-ethyl-2-methyl-4-hydroxy-3(2H)-furanone), maltol and derivatives, coumarin and derivatives, gamma-lactones, delta-lactones, methyl sorbate, divanillin, 4-hydroxy-2(or 5)-ethyl-5(or 2)-methyl-3(2H)furanone, 2-hydroxy-3-methyl-2-cyclopentenone, 3-hydroxy-4,5-dimethyl-2(5H)-furanone, fruit esters and fruit lactones, 4-(p-hydroxyphenyl)-2-butanone, 1,1-dimethoxy-2,2,5-trimethyl-4-hexan, 2,6-dimethyl-5-hepten-1-al, phenylacetaldehyde, and mixtures thereof.

6. The preparation according to claim 1 comprising:
  (a) 0.1 to 250 ppm of hesperetin, or a salt thereof.

7. The preparation according to claim 1, wherein the (a) hesperetin, or salt thereof, and the (b) one or more sweet-tasting substances in the preparation are in amounts such that the sweet impression of the preparation is enhanced by at least 40%, in comparison to a preparation with an otherwise identical composition without the (a) hesperetin, or salt thereof.

8. The preparation of claim 1, further comprising:
(d) one or more esters selected from the group consisting of lactic acid-$C_1$-$C_6$-esters, tartaric acid-di-$C_1$-$C_4$-esters, succinic acid-di-$C_1$-$C_4$-esters, malonic acid-di-$C_1$-$C_4$-esters, malic acid-di-$C_1$-$C_4$-esters, citric acid-di-$C_1$-$C_4$-esters, and citric acid-tri-$C_1$-$C_4$-esters; and optionally further comprises one or more 1,2-propylene glycol, dimethylsulphoxide, lactic acid, ethanol, ethanol/water mixtures, or mixtures thereof, as solvents.

9. The preparation of claim 1, further comprising at least one substance for masking or avoiding a bitter, metallic, chalky, acidic, or astringent taste impression.

10. The preparation of claim 1, further comprising at least one additional substance for enhancing a sweet, salty, or savory taste impression.

11. The preparation of claim 1, further comprising a 4-hydroxydihydrochalcone, or a salt thereof, other than (a) hesperetin, or a salt thereof, wherein the 4-hydroxydihydrochalcone has the following formula:

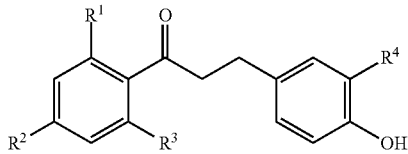

$R^1$, $R^2$, $R^3$, and $R^4$ are, independently of one another, H, OH, or $C_1$-$C_4$ alkoxy, provided that at least one of $R^1$, $R^2$, and $R^3$ is OH.

12. The preparation of claim 1, wherein the preparation is selected from the group consisting of:
(A) a confectionery;
(B) an alcoholic or non-alcoholic drink;
(C) a cereal or nut product;
(D) a milk product;
(E) a fruit and/or vegetable preparation;
(F) a product based on fat and oil or emulsions thereof; and
(G) an oral hygiene product.

13. The preparation of claim 1, wherein said preparation is spray-dried.

14. A preparation comprising:
(a) 0.1 to 500 ppm of hesperetin, or a salt thereof;
(b) sucrose;
wherein the (a) hesperetin, or salt thereof, and the (b) sucrose in the preparation are in amounts such that the sweet taste impression of the preparation is enhanced by at least 40%, in comparison to a preparation with an otherwise identical composition without the (a) hesperetin, or salt thereof.

15. A method for enhancing the sweet taste impression of a preparation comprising including in the preparation:
(a) 0.1 to 500 ppm of hesperetin, or a salt thereof; and
(b) one or more sweet-tasting substances selected from the group consisting of sucrose, lactose, glucose, D-tagatose, fructose, and sugar alcohols;
wherein the (a) hesperetin, or salt thereof, and the (b) one or more sweet-tasting substances in the preparation are in amounts such that the sweet taste impression of the preparation is enhanced by at least 20%, in comparison to a preparation with an otherwise identical composition without the (a) hesperetin, or salt thereof.

16. The method according to claim 15, wherein the (b) one or more sweet-tasting substances is selected from the group consisting of sucrose, lactose, glucose, D-tagatose, and fructose.

17. The method according to claim 15, wherein the (b) one or more sweet-tasting substances is sucrose.

18. The preparation according to claim 15, wherein the (a) hesperetin, or salt thereof, and the (b) one or more sweet-tasting substances in the preparation are in amounts such that the sweet taste impression of the preparation is enhanced by at least 40%, in comparison to a preparation with an otherwise identical composition without the (a) hesperetin, or salt thereof.

* * * * *